United States Patent
Weers et al.

(10) Patent No.: US 8,834,930 B2
(45) Date of Patent: Sep. 16, 2014

(54) PULMONARY DELIVERY OF A FLUOROQUINOLONE

(75) Inventors: Jeffry Weers, Belmont, CA (US); Thomas Tarara, Burlingame, CA (US)

(73) Assignee: Novartis AG, Basel (CH)

( * ) Notice: Subject to any disclaimer, the term of this patent is extended or adjusted under 35 U.S.C. 154(b) by 82 days.

(21) Appl. No.: 12/992,371

(22) PCT Filed: May 15, 2009

(86) PCT No.: PCT/US2009/044116
§ 371 (c)(1),
(2), (4) Date: Jan. 20, 2011

(87) PCT Pub. No.: WO2009/140587
PCT Pub. Date: Nov. 19, 2009

(65) Prior Publication Data
US 2011/0123626 A1    May 26, 2011

Related U.S. Application Data

(60) Provisional application No. 61/127,780, filed on May 15, 2008.

(51) Int. Cl.
*A61K 9/14* (2006.01)
*A61K 31/496* (2006.01)
*A61P 11/00* (2006.01)
*A61P 31/04* (2006.01)
*A61K 9/00* (2006.01)

(52) U.S. Cl.
CPC ............. *A61K 9/0075* (2013.01); *A61K 31/496* (2013.01)
USPC ..................................... 424/489; 514/253.07

(58) Field of Classification Search
None
See application file for complete search history.

(56) References Cited

U.S. PATENT DOCUMENTS

| | | | |
|---|---|---|---|
| 3,991,761 A | 11/1976 | Cocozza |
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,995,385 A | 2/1991 | Valentini et al. |

(Continued)

FOREIGN PATENT DOCUMENTS

| DE | 10305318 | 8/2004 |
|---|---|---|
| WO | 9501221 A1 | 1/1995 |

(Continued)

OTHER PUBLICATIONS

Li et al., "Investigation of excipient and processing on solid phase transformation and dissolution of ciprofloxacin," International Journal of Pharmaceutics 328, 2007, pp. 177-182.*

(Continued)

*Primary Examiner* — Rachael E Bredefeld
(74) *Attorney, Agent, or Firm* — Michael Mazza

(57) ABSTRACT

A composition for pulmonary administration comprises a fluoroquinolone betaine, such as ciprofloxacin betaine, and an excipient. In one version, the particles have a mass median aerodynamic diameter from about 1 μm to about 5 μm, and the fluoroquinolone has a half life in the lungs of at least 1.5 hours. The composition is useful in treating an endobronchial infection, such as *Pseudomonas aeruginosa*, and is particularly useful in treating cystic fibrosis.

22 Claims, 6 Drawing Sheets

(56) References Cited

U.S. PATENT DOCUMENTS

| | | | |
|---|---|---|---|
| 5,458,135 A | 10/1995 | Patton et al. | |
| 5,508,269 A | 4/1996 | Smith et al. | |
| 5,619,985 A | 4/1997 | Ohki et al. | |
| 5,785,049 A | 7/1998 | Smith et al. | |
| 5,855,913 A | 1/1999 | Hanes et al. | |
| 5,858,410 A | 1/1999 | Muller et al. | |
| 5,874,064 A | 2/1999 | Edwards et al. | |
| 5,976,574 A | 11/1999 | Gordon | |
| 5,985,248 A | 11/1999 | Gordon et al. | |
| 5,985,309 A | 11/1999 | Edwards et al. | |
| 6,001,336 A | 12/1999 | Gordon | |
| 6,051,256 A | 4/2000 | Platz et al. | |
| 6,077,543 A | 6/2000 | Gordon et al. | |
| 6,257,233 B1 | 7/2001 | Burr et al. | |
| 6,357,490 B1 | 3/2002 | Johnston et al. | |
| 6,358,530 B1 | 3/2002 | Eljamal et al. | |
| 6,372,258 B1 | 4/2002 | Platz et al. | |
| 6,503,480 B1 | 1/2003 | Edwards et al. | |
| 6,546,929 B2 | 4/2003 | Burr et al. | |
| 6,630,169 B1 | 10/2003 | Bot et al. | |
| 7,256,576 B2 | 8/2007 | Mandziuk et al. | |
| 7,326,691 B2 | 2/2008 | Duddu et al. | |
| 7,473,433 B2 | 1/2009 | Weikert et al. | |
| 7,516,741 B2 | 4/2009 | Glusker et al. | |
| 7,559,325 B2 | 7/2009 | Dunkley et al. | |
| 2002/0017295 A1 | 2/2002 | Weers et al. | |
| 2003/0094173 A1 | 5/2003 | Burr et al. | |
| 2003/0106827 A1 | 6/2003 | Cheu et al. | |
| 2003/0150454 A1 | 8/2003 | Burr et al. | |
| 2004/0042970 A1* | 3/2004 | Basu et al. | 424/46 |
| 2004/0105820 A1 | 6/2004 | Weers et al. | |
| 2004/0156792 A1 | 8/2004 | Tarara et al. | |
| 2004/0206350 A1 | 10/2004 | Alston et al. | |
| 2004/0254194 A1* | 12/2004 | Endermann et al. | 514/253.08 |
| 2005/0000518 A1 | 1/2005 | Dunkley et al. | |
| 2005/0074498 A1* | 4/2005 | Tarara et al. | 424/489 |
| 2006/0165606 A1 | 7/2006 | Tarara et al. | |
| 2006/0280691 A1 | 12/2006 | Wang | |
| 2007/0020199 A1* | 1/2007 | Platz et al. | 424/46 |
| 2007/0031490 A1 | 2/2007 | Loebenberg | |
| 2008/0160076 A1 | 7/2008 | Hochrainer et al. | |
| 2012/0010215 A1 | 1/2012 | Endermann et al. | |

FOREIGN PATENT DOCUMENTS

| | | | |
|---|---|---|---|
| WO | 9600610 A1 | 1/1996 | |
| WO | 9836825 A1 | 8/1998 | |
| WO | 9906855 A1 | 2/1999 | |
| WO | 9916419 A1 | 4/1999 | |
| WO | 9916420 A1 | 4/1999 | |
| WO | 9916422 A1 | 4/1999 | |
| WO | 0007572 A2 | 2/2000 | |
| WO | 0072904 A1 | 12/2000 | |
| WO | 0164254 A2 | 9/2001 | |
| WO | 0185136 A2 | 11/2001 | |
| WO | 0185137 A2 | 11/2001 | |
| WO | 0209674 A2 | 2/2002 | |
| WO | 02083220 A2 | 10/2002 | |
| WO | 02087542 A1 | 11/2002 | |
| WO | 2004060351 A2 | 7/2004 | |
| WO | 2004069253 A1 | 8/2004 | |
| WO | 2005044226 A2 | 5/2005 | |
| WO | 2006002178 A1 | 1/2006 | |
| WO | WO 2006033713 | 3/2006 | |
| WO | 2006125132 A2 | 11/2006 | |
| WO | 2007022830 A1 | 3/2007 | |

OTHER PUBLICATIONS

International Search Report, PCT/US2009/044116 (Oct. 9, 2009).
Abbott J et al "Treatment compliance in adults with cystic fibrosis" Thorax 49:115-120 (1994).
Ballmann Manfred et al "Long term follow up of changes in FEV1 and treatment intensity during *Pseudomonas aeruginosa* colonisation in patients with cystic fibrosis" Thorax 53:732-737 (1998).
Barrett Elliott P et al "The Determination of Pore Volume and Area Distributions in Porous Substances. I. Computations from Nitrogen Isotherms" J Amer Chem Soc 73:373-380 (1951).
Brummett Re "Drug-induced Ototoxicity" Drugs 19:412-428 (1980).
Collins Francis S "Cystic Fibrosis: Molecular Biology and Therapeutic Implications" Science 256:774-779 (1992).
Conley J et al "Aerosol delivery of liposome-encapsulated ciprofloxacin: aerosol characterization and efficacy against *Francisella tularensis* infection in mice" Antimicrob Agents Chemother 41(6):1288-1292 (1997).

Conway SP et al "Compliance with treatment in adult patients with cystic fibrosis" Thorax 51:29-33 (1996).

Corey Mary et al "Longitudinal analysis of pulmonary function decline in patients with cystic fibrosis" J Pediatr 131:809-814 (1997).

Patient Registry Annual Data Report 2003, Cystic Fibrosis Foundation Bethesda, MD (2004).

Dalhoff A "Interaction of Quinolones with Host-Parasite Relationship" Quinolone Antibacterials, Handbook of Experimental Pharmacology, Kuhlmann J et al eds, Springer Verlag, NY, Ch 8 127:233-257 (1998).

Dalhoff A et al "In Vitro Antibacterial Activity and Pharmacodynamics of New Quinolones" Eur J Clin Microbiol Infect Dis 22:203-221 (2003).

Dalhoff Axel et al "Immunomodulatory effects of quinolones" Lancet 3:359-371 (2003).

Dalhoff A "Immunomodulatory Activities of Fluoroquinolones" Infection 33(S2):55-70 (2005).

Davis Pamela B et al "Cystic Fibrosis" Am J Respir Crit Care Med 154:1229-1256 (1996).

Davis Pamela B et al "Identifying Treatments That Halt Progression of Pulmonary Disease in Cystic Fibrosis" Pediatr Res 41:161-165 (1997).

Demko Catherine A et al "Gender Differences in Cystic Fibrosis: *Pseudomonas aeruginosa* Infection" J Clin Epidemiol 48(8):1041-1049 (1995).

Emerson Julia et al "*Pseudomonas Aeruginosa* and Other Predictors of Mortality and Morbidity in Young Children With Cystic Fibrosis" Pediatr Pulmonol 34:91-100 (2002).

Fitzsimmons Stacey C "The changing epidemiology of cystic fibrosis" J Pediatr 122(1):1-9 (1993).

Forrest A et al "Pharmacodynamics of intravenous ciprofloxacin in seriously ill patients" Antimicrob Agents Chemother 37(5):1073-1081 (1993).

Fuchs Henry J et al "Effect of Aerosolized Recombinant Human DNase on Exacerbations of Respiratory Symptoms and on Pulmonary Function in Patients with Cystic Fibrosis" N Engl J Med 331(10):637-642 (1994).

Gibson Ronald L et al "Pathophysiology and Management of Pulmonary Infections in Cystic Fibrosis" Am J Respir Crit Care Med 168:918-951 (2003).

Henry Richard L et al "Mucoid *Pseudomonas aeruginosa* is a Marker of Poor Survival in Cystic Fibrosis" Pediatr Pulmonol 12:158-161 (1992).

"Guide for the Evaluation of Hearing Handicap" JAMA 241(19):2055-2059 (1979).

Kerem Eitan et al "Prediction of Mortality in Patients with Cystic Fibrosis" N Engl J Med 326(18):1187-1191 (1992).

König Peter et al "Short-Term and Long-Term Effects of Albuterol Aerosol Therapy in Cystic Fibrosis: A Preliminary Report" Pediatr Pulmonol 20:205-214 (1995).

Konstan Michael W et al "Effect of High-Dose Ibuprofen in Patients with Cystic Fibrosis" N Engl J Med 332:848-854 (1995).

MacLusky Ian B et al "Long-Term Effects of Inhaled Tobramycin in Patients with Cystic Fibrosis Colonized with *Pseudomonas aeruginosa*" Pediatr Pulmonol 7:42-48 (1989).

Pamukcu A et al "Effects of *Pseudomonas aeruginosa* Colonization on Lung Function and Anthropometric Variables in Children with Cystic Fibrosis" Pediatr Pulmonol 19:10-15 (1995).

Pedersen Svend Stenvang et al "Role of alginate in infection with mucoid *Pseudomonas aeruginosa* in cystic fibrosis" Thorax 47:6-13 (1992).

(56) References Cited

OTHER PUBLICATIONS

Pesci Everett C et al "Quinolone signaling in the cell-to-cell communication system of *Pseudomonas aeruginosa*" Proc Natl Acad Sci USA 96:11229-11234 (1999).

Pharmacopeial Forum 29(5):1733 (2003).

Ramsey Bonnie W et al "Intermittent Administration of Inhaled Tobramycin in Patients with Cystic Fibrosis" N Engl J Med 340(1):23-30 (1999).

Reisman John J et al "Role of conventional physiotherapy in cystic fibrosis" J Pediatr 113:632-636 (1988).

Rosenfeld Margaret et al "Aerosolized Antibiotics for Bacterial Lower Airway Infections: Principles, Efficacy, and Pitfalls" Clin Pulm Med 4(2):101-112 (1997).

Sagel Scott D "Identifying Novel Endpoints for Cystic Fibrosis Clinical Trials" Adv Pediatr Ch 6 52:115-127 (2005).

Touw DJ et al "Inhalation of antibiotics in cystic fibrosis" Eur Respir J 8:1594-1604 (1995).

Weers Jeffry et al "High Dose Inhaled Powder Delivery: Challenges and Techniques" Respir Drug Deily IX p. 281-288 (2004).

Winnie Glenna B et al "Respiratory Tract Colonization with *Pseudomonas aeruginosa* in Cystic Fibrosis: Correlations Between Anti-*Pseudomonas aeruginosa* Antibody Levels and Pulmonary Function" Pediatr Pulmonol 10:92-100 (1991).

Wong JP et al "Liposome-Encapsulated Ciprofloxacin for the Prevention and Treatment of Infectious Diseases Caused by Intracellular Pathogens" Liposomes in Biomedical Applications, Shek ed, Harwood Academic Pub, Ch 7 p. 105-120 (1995).

Brunauer Stephen et al "Adsorption of Gases in Multimolecular Layers" J Amer Chem Soc 60:309-319 (1938).

\* cited by examiner

PULMONARY DELIVERY OF A FLUOROQUINOLONE

This application is a 35 USC §371 application of International Application No. PCT/US2009/044116 filed May 15, 2009, designating the United States, which claims priority to U.S. Application No. 61/127,780 filed May 15, 2008, and which is hereby incorporated by reference in its entirety.

BACKGROUND

One or more embodiments of the present invention comprise pharmaceutical compositions comprising one or more fluoroquinolones, such as ciprofloxacin. One or more embodiments of the present invention comprise powders comprising the betaine form of one or more fluoroquinolones, such as ciprofloxacin betaine. One or more embodiments of the present invention comprise methods of making, using and/or administering such pharmaceutical compositions, dosage forms thereof and devices, systems and methods for the pulmonary delivery of such compositions.

This invention relates to compositions and methods for treating bacterial infections, and has particular reference to the treatment of cystic fibrosis (CF), non-CF bronchiectasis, and acute exacerbations in chronic obstructive pulmonary disease.

Cystic fibrosis is the most common life-shortening genetic disease in the United States and Northern Europe, affecting approximately 30,000 individuals in the United States and a similar number of individuals in Western Europe. The genetic defect in this autosomal recessive disease is a mutation in the CF transmembrane conductance regulator (CFTR) gene, which codes for a chloride-channel protein. Persons with CF typically suffer from chronic endobronchial infections, sinusitis, and malabsorption due to pancreatic insufficiency, increased salt loss in sweat, obstructive hepatobiliary disease, and reduced fertility Respiratory disease is a major cause of morbidity and accounts for 90% of mortality in persons with CF. Lung function (measured as forced expiratory volume at 1 second (FEV1% predicted) is a significant predictor of survival in CF. Two-year survival for a given population of persons with CF is reduced 2-fold with each 10% reduction in FEV1% predicted, and persons with FEV1 below 30% of predicted have a 2-year survival below 50% (Kerem, E. et al., "Prediction of Mortality in Patients with Cystic Fibrosis," N Engl J Med 326:1187-1191 (1992)). Rates of lung function loss vary both between individuals and over time for a given individual. Retrospective longitudinal analyses show rates of decline ranging from less than 2% of FEV1% predicted per year to greater than 9% FEV1% predicted per year, with overall rate of decline strongly associated with age of death.

CF patients suffer from thickened mucus believed to be caused by perturbed epithelial ion transport that impairs lung host defenses, resulting in increased susceptibility to early endobronchial infections with *Staphylococcus aureus, Haemophilus influenzae*, and *Pseudomonas aeruginosa*. By adolescence, a majority of persons with CF have *P. aeruginosa* present in their sputum. Chronic endobronchial infections, particularly with *P. aeruginosa*, provoke a persistent inflammatory response in the airway that accelerates progressive obstructive disease characterized by diffuse bronchiectasis; Winnie, G. B. et al., "Respiratory Tract Colonization with *Pseudomonas aeruginosa* in Cystic Fibrosis: Correlations Between AxAi-*Pseudomonas aeruginosa* Antibody Levels And Pulmonary Function," Pediatr Pulmonol 10:92-100 (1991). A link between acquisition of chronic endobronchial *P. aeruginosa* infection, lung inflammation, loss of lung function, and ultimate death is suggested by significantly decreased survival associated with chronic *P. aeruginosa* infection (Henry, R. L. et al., "Mucoid *Pseudomonas aeruginosa* is a Marker of Poor Survival in Cystic Fibrosis," Pediatr Pulmonol 12(3):158-61 (1992)), and by the significant association of early acquisition of chronic *P. aeruginosa* infection and childhood mortality (Demko, C A. et al., "Gender Differences in Cystic Fibrosis: *Pseudomonas aeruginosa* Infection," J Clin Epidemiol 48:1041-1049 (1995)).

Various therapies have been attempted to treat *P. aeruginosa* in CF patients. These therapies aim to either suppress bacterial loads in the lung or suppress resulting inflammation. Such therapies have been shown to reduce rates of lung function decline in infected patients, but have shortcomings.

Historically, the standard therapy for treatment of *P. aeruginosa* endobronchial infections was 14 to 21 days of parenteral antipseudomonal antibiotics, typically including an aminoglycoside. However, the inability of these agents to pass efficiently from the bloodstream into the lung tissue and airway secretions resulted in sub-therapeutic concentrations at the target site. As a result, repeated exposure to parenteral aminoglycosides led to development of resistant isolates which were associated with production of more mucus and a variety of virulence factors. To obtain adequate drug concentrations at the site of infection with parenteral administration, serum levels approaching those associated with nephro-, vestibule-, and oto-toxicity were required ("American Academy of Otolaryngology. Guide for the evaluation of hearing handicap," JAMA 241(19):2055-9 (1979); Brummett, R. E., "Drug-induced ototoxicity," Drugs 19:412-28 (1980)).

Inhalation administration of antibiotics, such as aminoglycosides has offered an attractive alternative, delivering high concentrations of antibiotic directly to the site of infection in the endobronchial space while minimizing systemic bioavailability.

For example, TOBI®, which comprises the aminoglycoside Tobramycin, is approved for inhalation therapy for the treatment of endobronchial infections in CF patients [NDA 50-753]. Since its approval, TOBI® (Novartis, Basel, Switzerland), has become the standard of care in CF patients chronically colonized with *P. aeruginosa*. Patients receive a 300 mg nominal dose, administered with a standard jet nebulizer twice daily. Patients receive a 28 day "on" therapy followed by a 28 day "off" period, to reduce the potential for development of resistant bacterial strains. However, of the 300 mg dose, only approximately 10% or 30 mg is delivered to the lung. Clinical studies with TOBI® have shown that inhaled tobramycin has dramatically reduced systemic side-effects. The aerosol administration of a 5 ml dose of a formulation containing 300 mg of tobramycin in quarter normal saline for the suppression of *P. aeruginosa* in the endobronchial space of a patient is disclosed in U.S. Pat. No. 5,508,269, the disclosure of which is incorporated herein in its entirety by this reference.

There are limitations on the use of tobramycin in CF patients. Systemic tobramycin given by IV injection can have serious adverse effects including renal and ototoxicity. Nebulized liquids may possess issues related to the preparation and administration thereof, as well as the development of increased resistance (i.e., increase in minimal inhibitory concentration value, MIC) for *P. aeruginosa* during treatment. The treatment regimen of one month on and one month off therapy has to be maintained to avoid the development of resistance allowing the susceptible pathogens to repopulate, despite the risk of deterioration in pulmonary function. Long-term impact of inhaled aminoglycosides on kidney function is not well understood. The 5 mL dose requires about 15-20 min to administer with additional time for set-up and nebulizer cleaning. Nebulization may have other disadvantages, such as cost, efficiency and reproducibility, risk of bacterial contamination, and the lack of portability (need for bulky compressors or gas cylinders and power sources).

In addition to inhaled antibiotics such as the commercially available TOBI product, a variety of other chronic therapies are routinely prescribed to reduce the destructive cycles of obstruction, infection, and inflammation in the CF lung. Aggressive airway clearance therapy, inhaled bronchodilators, and mucolytics such as recombinant human dornase alpha are all prescribed chronically, creating a potential for significant treatment burden for persons with CF. Many CF patients spend more than four hours daily receiving therapy. Not surprisingly, it has been shown that adherence to treatment therapies is a significant problem for CF patients and that lack of compliance can vary by specific treatment. In view of the extended treatment times, any regimens that can significantly reduce the time of administration, and the convenience associated with administration (e.g., device portability and ease of use) are advantageous, potentially improving patient compliance and outcomes. As well, the development of alternative inhaled antibiotic formulations which can be administered in the TOBI off-period may provide a treatment alternative which does not require repopulation of susceptible pathogens and loss in pulmonary function.

Ciprofloxacin is a synthetic, fluorinated carboxyquinolone with a broad spectrum of activity. Ciprofloxacin selectively inhibits bacterial deoxyribonucleic acid (DNA) synthesis by acting on DNA gyrase and topoisomerase IV. These essential enzymes control DNA topology and assist in DNA replication, repair, and transcription. Ciprofloxacin has been shown to have good in-vitro bactericidal activity against a number of pathogens that cause respiratory infections, including *Mycobacterium tuberculosis, Mycobacterium avium-M. intracellulare, Bacillus anthracis, Hemophilus influenzae, Neisseria meningitidis*, and *Pseudomonas aeruginosa*. Ciprofloxacin is currently regarded as one of the most if not the most active fluoroquinolone against *P. aeruginosa*, and is highly bactericidal. Oral and intravenous forms of ciprofloxacin have been used clinically to treat respiratory tract infections.

Despite the success with ciprofloxacin, there are some factors which limit the drug's clinical utility for treating lung infections, such as its poor solubility at physiological pH, bitter taste in solution, and rapid renal clearance. For example, in order to administer a 500 mg intravenous dose, the drug must first be diluted to <2 mg/ml and infused slowly to avoid precipitation at the site of injection. Ciprofloxacin administered intravenously or orally also has unfavorable pharmacokinetic profiles in the lower respiratory tract, including a relatively short elimination half-life of 1.0 to 1.6 hr, and a low area under the concentration-time curve of 43 to 113 mg h/L.

Inhalation of ciprofloxacin by patients in need thereof, such as CF patients, COPD patients and anthrax patients, would be expected to result in high bactericidal concentrations in the airways. Even sub-inhibitory concentrations of ciprofloxacin affect the virulence of *P. aeruginosa* (quorum sensing), and potentially reduce the incidence of chronic airway infections in CF patients. Reducing the airway bacterial load and potentially slowing re-infection may translate into improved lung function and contribute to an improved long-term prognosis. Moreover, inhalation of ciprofloxacin may overcome the potential for renal insufficiency noted following treatment with aminoglycosides.

However, effective pulmonary delivery of ciprofloxacin has proven to be difficult. A challenge associated with the delivery of antiinfectives such as ciprofloxacin to the lungs is the potential for rapid clearance of the drug via: (a) mucociliary clearance from the airways; (b) absorption of drug into the systemic circulation; (c) clearance via pulmonary macrophages. Following intratracheal administration, soluble ciprofloxacin hydrochloride is rapidly absorbed from the lungs into the systemic circulation with a half-life of just 0.2 hr (Wong J P, Cherwonogroszky J W, DiNinno V L et al: Liposome-encapsulated ciprofloxacin for the prevention and treatment of infectious diseases caused by intracellular pathogens. In: "Liposomes in Biomedical Applications" (Florence A T, Gregoriadis G, eds) Harwood Academic Press, Amsterdam, 1995, p 105-120). This is too short to achieve effective treatment of endobronchial *P. aeruginosa* infections, and presents a significant constraint for formulation development.

In order to overcome the rapid clearance of ciprofloxacin hydrochloride from the lungs, researchers have explored encapsulation in controlled release carriers, such as liposomes. For example Wong and coworkers showed significant increases in lung residence time with liposomal ciprofloxacin, which translated into effective treatment of *Francicella tularensis* infections in a rodent model. Limitations for liposomal delivery of ciprofloxacin via nebulization include: (a) extended administration times due to low drug loadings and limits on dispersion concentrations acceptable for nebulization (viscosity constraint); (b) limited control of the release kinetics. In the Wong study, a standard jet nebulizer was used. Such nebulizers typically provide a flow rate of 0.1 to 0.2 ml/min. At the drug content of 10-40 μg/ml, the flow rate was 1 to 8 μg/min. Assuming about 10% delivery efficiency, only 0.1 to 0.8 μg/min would be delivered to the lungs. Hence, delivery of lung doses greater than 10 mg is not practical using this model.

The utilization of polymeric carriers as a means to prolong lung residence time of ciprofloxacin hydrochloride has not been advanced into clinical practice. Concerns remain with respect to the slow clearance of polymeric carriers from the lungs.

At pH values below $pK_1$ (6.0) and above $pK_2$ (8.8), ciprofloxacin has a net charge and is highly soluble. In the pH range between 6.0 and 8.8, the compound is zwitterionic, and is practically insoluble (solubility at pH 7 is 60 μg/ml). Studies have demonstrated that the zwitterionic form, ciprofloxacin betaine, has an extended residence time in the lungs (Endermann R, Labischinski H, Ladel C et al: Treatment of bacterial diseases of the respiratory organs. US Patent Appl US 2004/0254194 A1). However, Endermann et al do not teach the administration of ciprofloxacin betaine in a form that is easily, effectively, and reproducibly deliverable to a patient.

In addition, one of the key challenges faced in the pulmonary delivery of antiinfectives is the magnitude of the therapeutic lung doses (>10 mg) that are required. Asthma therapeutics (e.g., bronchodilators and corticosteroids) dominate the aerosol delivery market. As shown in FIG. 1, asthma drugs are highly potent with delivered lung doses of less than about 100 micrograms (μg.) See also Weers J, Clark A, Challoner P: High dose inhaled powder delivery: challenges and techniques. In: "Respiratory Drug Delivery IX" (R N Dalby, P R Byron, J Peart, J D Suman, S J Farr, Eds) Davis Healthcare Intl Publishing, River Grove, Ill., 2004, pp 281-288.

Thus, existing therapies suffer from several deficiencies. In view of the known systems for administering antibiotic aerosols, there remains a need for high efficiency and more convenient systems. One or more embodiments of the present invention satisfy one or more of these needs.

SUMMARY OF THE INVENTION

The present invention satisfies these existing needs.

In one aspect of the invention, a pharmaceutical formulation for pulmonary delivery comprising a fluoroquinolone, such as ciprofloxacin moxifloxacin, or levofloxacin, is provided in a form where it may be effectively delivered to the lungs.

In another aspect of the invention, a powder composition for pulmonary administration comprises particles comprising a fluoroquinolone and an excipient. The particles have a mass median aerodynamic diameter from about 1 µm to about 5 µm. The fluoroquinolone has a half life in the lungs of at least 1.5 hours.

In another aspect of the invention, a powder composition for pulmonary administration comprises particles comprising a fluoroquinolone and an excipient. The particles have a mass median aerodynamic diameter from about 1 µm to about 5 µm and a bulk density of less than about 0.6 g/cm$^3$ and a rugosity of from about 3 to about 10. The fluoroquinolone has a half life in the lungs of at least 1.5 hours.

In another aspect of the invention, a composition for pulmonary administration comprises particles comprising a fluoroquinolone betaine and an excipient.

In another aspect of the invention, a composition for pulmonary administration comprises particles comprising a fluoroquinolone betaine and an excipient, wherein the particles are powder particles having a rugosity of from about 3 to about 10.

In another aspect of the invention, a composition for pulmonary administration comprises ciprofloxacin betaine, wherein the ciprofloxacin betaine consists essentially of ciprofloxacin betaine 3.5 hydrate.

In another aspect of the invention, a unit dosage form for pulmonary administration comprises a receptacle containing a composition in powder form, wherein the composition comprises a fluoroquinolone betaine.

In another aspect of the invention, a unit dosage form for pulmonary administration comprises a receptacle containing a composition in powder form, wherein the composition comprises a fluoroquinolone betaine. The particles have a mass median aerodynamic diameter from about 1 µm to about 5 µm and a bulk density of less than about 0.6 g/cm$^3$ and a rugosity of from about 3 to about 10.

In another aspect of the invention, a delivery system comprises a unit dosage form comprising a receptacle containing a composition in powder form, wherein the composition comprises a fluoroquinolone betaine. The delivery system further comprises a dry powder inhaler comprising a chamber adapted to receive the capsule.

In another aspect of the invention, a method of making particles for pulmonary delivery comprises providing a liquid feedstock comprising a fluoroquinolone betaine and an excipient. The liquid is removed from the feedstock to produce particles comprising the fluoroquinolone betaine and the excipient. The resulting particles have a mass median aerodynamic diameter from about 1 µm to about 5 µm.

In another aspect of the invention, a method of making particles for pulmonary delivery comprises providing a liquid feedstock comprising a fluoroquinolone betaine and an excipient. The liquid is removed from the feedstock to produce particles comprising the fluoroquinolone betaine and the excipient. The resulting particles have a mass median aerodynamic diameter from about 1 µm to about 5 µm, a bulk density of less than about 0.6 g/cm$^3$, and a rugosity of from about 3 to about 10.

In another aspect of the invention, a method of treating an endobronchial infection comprises administering by inhalation an effective amount of a composition to a patient in need thereof, wherein the composition comprises particles comprising a fluoroquinolone betaine and at least one excipient and wherein the particles have a mass median aerodynamic diameter from about 1 µm to about 5 µm.

In another aspect of the invention, a method of treating an endobronchial infection comprises administering by inhalation an effective amount of a composition to a patient in need thereof, wherein the composition comprises particles comprising a fluoroquinolone betaine and at least one excipient and wherein the particles have a mass median aerodynamic diameter from about 1 µm to about 5 µm, a bulk density of less than about 0.6 g/cm$^3$, and a rugosity of from about 3 to about 10.

In another aspect of the invention, a method of treating an endobronchial infection comprises administering by inhalation an effective amount of a composition to a patient in need thereof, wherein the composition comprises particles comprising a fluoroquinolone betaine and at least one excipient and wherein the particles have a mass median aerodynamic diameter from about 1 µm to about 5 µm, and wherein the effective amount is administered in four or fewer inhalations, preferably three, more preferably one.

In another aspect of the invention, a method of treating an endobronchial infection comprises administering by inhalation an effective amount of a composition to a patient in need thereof, wherein the composition comprises power particles comprising a fluoroquinolone and at least one excipient and wherein the particles have a mass median aerodynamic diameter from about 1 µm to about 5 µm, and wherein the fluoroquinolone has a half-life in the lungs of at least 1.5 hours.

In another aspect of the invention, a method of treating an endobronchial infection comprises administering by inhalation an effective amount of a composition to a patient in need thereof, wherein the composition comprises power particles comprising a fluoroquinolone and at least one excipient and wherein the particles have a mass median aerodynamic diameter from about 1 µm to about 5 µm, a bulk density of less than about 0.6 g/cm$^3$, and a rugosity of from about 3 to about 10, and wherein the fluoroquinolone has a half-life in the lungs of at least 1.5 hours.

One or more embodiments of the present invention comprise a powder composition of a fluoroquinolone betaine, such as ciprofloxacin betaine, which can be loaded into a size No. 2 capsule (or smaller volume), and delivers, via pulmonary administration, a lung dose of at least about 10 mg in a single inhalation.

One or more embodiments of the present invention comprise a powder composition of a fluoroquinolone betaine, such as ciprofloxacin betaine, which can be loaded into a size No. 2 capsule (or smaller volume), and delivers, via pulmonary administration, a therapeutic lung dose in three or four inhalations or less.

One or more embodiments of the present invention comprise a powder composition of a fluoroquinolone betaine, such as ciprofloxacin betaine, which can be loaded into a size No. 2 capsule (or smaller volume), and delivers, via pulmonary administration, a therapeutic lung dose in two inhalations or less.

One or more embodiments of the present invention comprise a powder composition of a fluoroquinolone betaine, such as ciprofloxacin betaine, which can be loaded into a size No. 2 capsule (or smaller volume), and delivers, via pulmonary administration, a therapeutic lung dose in a single inhalation.

In one or more embodiments of the present invention, a powder composition comprising particles comprising 50% to 70% w/w crystalline ciprofloxacin betaine coated with a porous layer of a long chain saturated phosphatidylcholine, wherein the particles have a mass median diameter of between 1 and 5 microns, a mass median aerodynamic diameter of between 1 and 5 microns, and a rugosity (Sv) of between 3 and 10.

In one or more embodiments of the present invention, a powder composition comprises particles comprising crystalline ciprofloxacin betaine 3.5 hydrate with a residual moisture content of between 10% and 15% w/w, and a pH on reconstitution of between 6.0 and 8.8.

In one or more embodiments of the present invention, a powder composition comprises particles comprising crystalline ciprofloxacin betaine 3.5 hydrate and an excipient, wherein the specific surface area of the particles is between 8 and 20 m$^2$/g, the particle porosity is between 5 to 20 cm$^3$/g, and the rugosity ($S_v$) is between 3 and 10.

In one or more embodiments of the present invention, a powder composition comprises particles comprising crystalline ciprofloxacin betaine 3.5 hydrate coated with a porous layer of excipient, wherein the specific surface area of the particles is between 8 and 20 m$^2$/g, the particle porosity is between 5 to 20 cm$^3$/g, and the rugosity ($S_v$) is between 3 and 10.

In one or more embodiments of the present invention, a powder comprising a fluoroquinolone is filled into a receptacle, such as a capsule, the powder having a bulk density as determined by uniaxial compaction is in the range from 0.1 to 0.6 g/cm$^3$.

In one or more embodiments of the present invention, a powder comprising a fluoroquinolone is filled into a receptacle, such as a capsule, the powder having a bulk density as determined by uniaxial compaction is less than 0.6 g/cm$^3$ and more preferably in the range from 0.2 to 0.5 g/cm$^3$.

In one or more embodiments of the present invention, a pharmaceutical composition comprises a powder comprising a therapeutically effective amount of ciprofloxacin betaine and pharmaceutically acceptable excipients, wherein the powder comprises particles comprising from 50% to 70% w/w crystalline ciprofloxacin betaine and 30% to 50% w/w of a 2:1 mol:mol ratio of distearoylphosphatidylcholine to calcium chloride dihydrate.

In one or more embodiments of the present invention, a unit dosage form, comprises a container containing a pharmaceutical composition comprising a powder comprising a therapeutically effective amount of ciprofloxacin betaine and pharmaceutically acceptable excipients, wherein the powder comprises particles comprising from 50% to 70% w/w crystalline ciprofloxacin betaine and 30% to 50% w/w of a 2:1 mol:mol ratio of distearoylphosphatidylcholine to calcium chloride dihydrate.

In one or more embodiments of the present invention, a delivery system, comprising a dry powder inhaler and a pharmaceutical composition comprising a powder comprising a therapeutically effective amount of ciprofloxacin betaine and pharmaceutically acceptable excipients, wherein the powder comprises particles comprising from 50% to 70% w/w crystalline ciprofloxacin betaine and 30% to 50% w/w of a 2:1 mol:mol ratio of distearoylphosphatidylcholine to calcium chloride dihydrate.

In one or more embodiments of the present invention, a method of making spray-dried particles comprises suspending crystalline ciprofloxacin betaine in a liquid comprising submicron emulsion droplets stabilized with pharmaceutically acceptable excipients to form a feedstock, and spray-drying the feedstock to produce spray-dried particles, wherein the particles comprise ciprofloxacin betaine coated with a porous layer of the pharmaceutically acceptable excipients, wherein the particles have a mass median diameter of between 1 and 5 microns, a mass median aerodynamic diameter of between 1 and 5 microns, and a rugosity (Sv) of between 3 and 10.

In one or more embodiments of the present invention, a method of making spray-dried particles comprises suspending crystalline ciprofloxacin betaine in a liquid comprising submicron emulsion droplets stabilized with pharmaceutically acceptable excipients to form a feedstock, and spray-drying the feedstock to produce spray-dried particles, wherein the particles comprise 3.5 hydrate form of ciprofloxacin betaine crystals coated with a porous layer of the pharmaceutically acceptable excipients, wherein the particles have a mass median diameter of between 1 and 5 microns, a mass median aerodynamic diameter of between 1 and 5 microns, and a rugosity (Sv) of between 3 and 10.

In one or more embodiments of the present invention, a method of treating pulmonary infections comprises administering by inhalation an effective amount of a composition comprising ciprofloxacin betaine to a patient in need thereof, wherein the composition comprises a powder comprising particles comprising 50-70% w/w ciprofloxacin betaine, and having a mass median diameter of between 1 and 5 microns, a mass median aerodynamic diameter of between 1 and 5 microns, and a rugosity (Sv) of between 3 and 10.

In one or more embodiments of the present invention, powders for pulmonary delivery are prepared by spray-drying from an emulsion-based feedstock on a Niro Mobile Minor scale dryer with an inlet temperature of 125 to 145° C. and an outlet temperature of between 60 and 80° C. The resulting particles have a plate-like morphology consistent of the drug substance, and are coated with a porous layer of excipients, wherein the rugosity (Sv) of the particles is between 3 and 10.

In one or more embodiments of the present invention, powders comprising particles comprising a fluoroquinolone are loaded into a No. 2 hydroxypropylmethylcellulose (HPMC) capsule with a fill mass of between 20 and 60 mg.

In one or more embodiments of the present invention, powders of the present invention comprise ciprofloxacin betaine as the drug substance, and achieve a lung half-life of greater than 3 hours, with concomitant improved efficacy against *P. aeruginosa*.

In one or more embodiments of the present invention, powders comprising ciprofloxacin provide treatment of *Pseudomonas aeruginosa* infections in CF patients in an off-month following the on-month for TOBI® tobramycin inhalation.

In one or more embodiments of the present invention, powders comprising ciprofloxacin provide treatment of infections in COPD patients.

In one or more embodiments of the present invention, powders comprising ciprofloxacin provide treatment of anthrax infections.

In one or more embodiments of the present invention, spray-dried ciprofloxacin powders positively impact the quality of life of CF patients by improving long-term lung function (FEV$_1$), while providing low administration time, such as less than five minutes, with a portable inhaler.

In one or more embodiments of the present invention, the $AUC_{sputum}/AUC_{plasma}$ ratio afforded by effective targeting of the ciprofloxacin betaine to the lungs is greater than 50, preferably greater than 100, and more preferably greater than 250.

In one or more embodiments of the present invention, the present invention provides particles comprising ciprofloxacin betaine which need not be blended with coarse lactose carrier particles to provide excellent powder fluidization and dispersion.

In one or more embodiments of the present invention, a composition comprising a fluoroquinolone betaine, such as ciprofloxacin betaine, has a lung delivery efficiency from portable, passive dry powder inhalers of greater than 30%, 40%, 50%, 60% or more.

In one or more embodiments of the present invention, a drug/device combination comprises a composition comprising afluoroquinolone betaine, such as ciprofloxacin betaine which can deliver target lung doses (>10 mg) in a single inhalation.

In one or more embodiments of the present invention, the present invention provides a therapeutic formulation of ciprofloxacin betaine for the treatment of cystic fibrosis, non-CF bronchiectasis, hospital-acquired pneumonia, acute exacerbations of chronic bronchitis, or anthrax.

Further embodiments comprise any two or more of any of the foregoing features, aspects, versions or embodiments.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DRAWINGS

Embodiments of the present invention are further described in the description of invention that follows, in reference to the noted plurality of non-limiting drawings, wherein:

FIG. 1 is a plot of approximate lung doses required for various therapeutics delivered via the pulmonary route. Also shown are the maximum lung doses that can be delivered in a single inhalation from portable aerosol devices. Antiinfectives, such as aminoglycosides and fluoroquinolones, require large lung doses (10-100 mg), which limits the potential formulation/device options, to nebulizers and capsule-based dry powder inhalers.

FIG. 2 is a plot of the aqueous solubility of ciprofloxacin in 0.15 M KCl as a function of pH. The zwitterionic ciprofloxacin betaine is present at pH values between 6.0 and 8.8. The water solubility for the ciprofloxacin betaine at neutral pH is very low (70 µg/ml), making it suitable for formulation using the suspension-based emulsion manufacturing process which produces crystals coated with a porous layer of hydrophobic phospholipid.

Figures 6, 7:
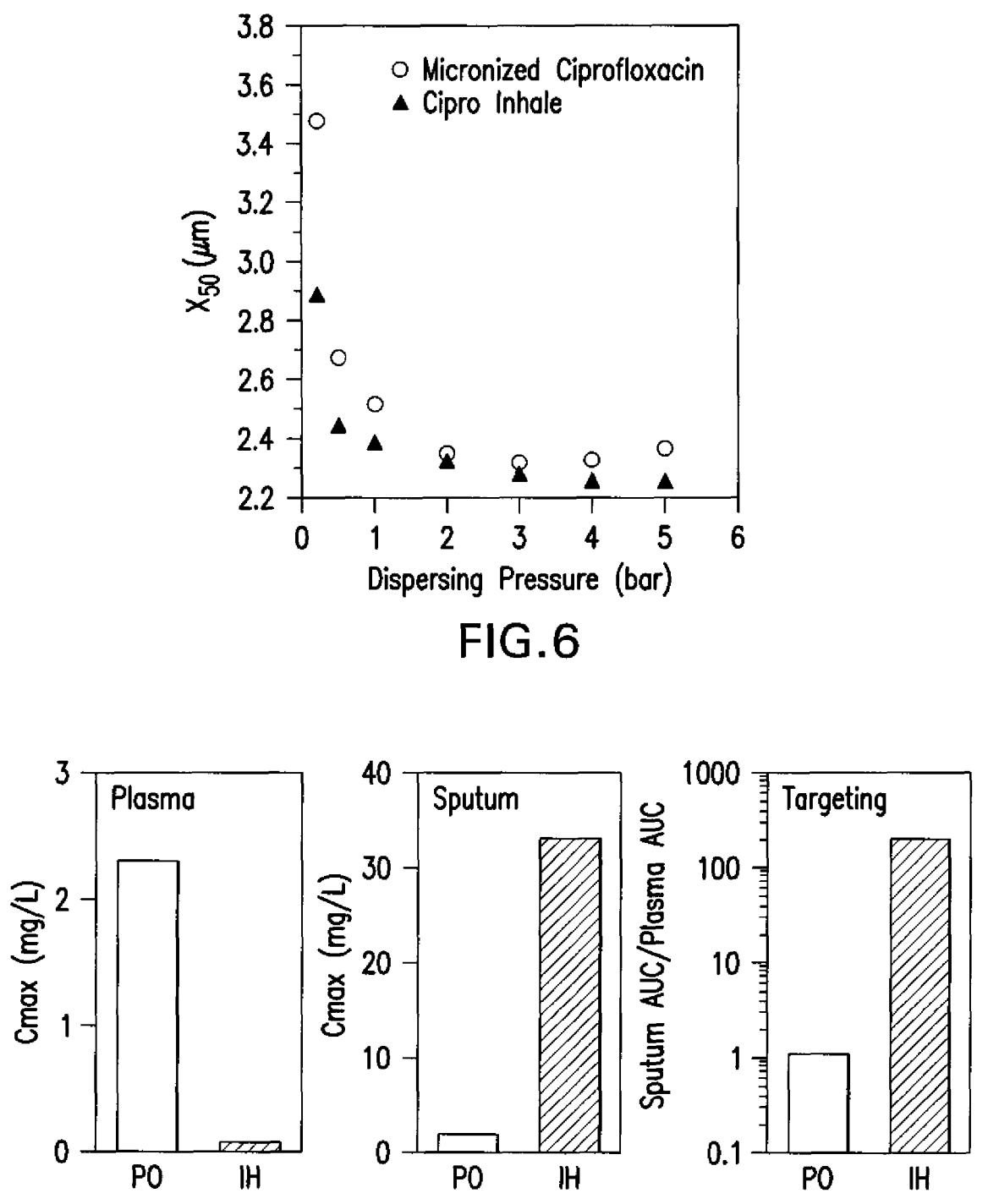
Figure 1:
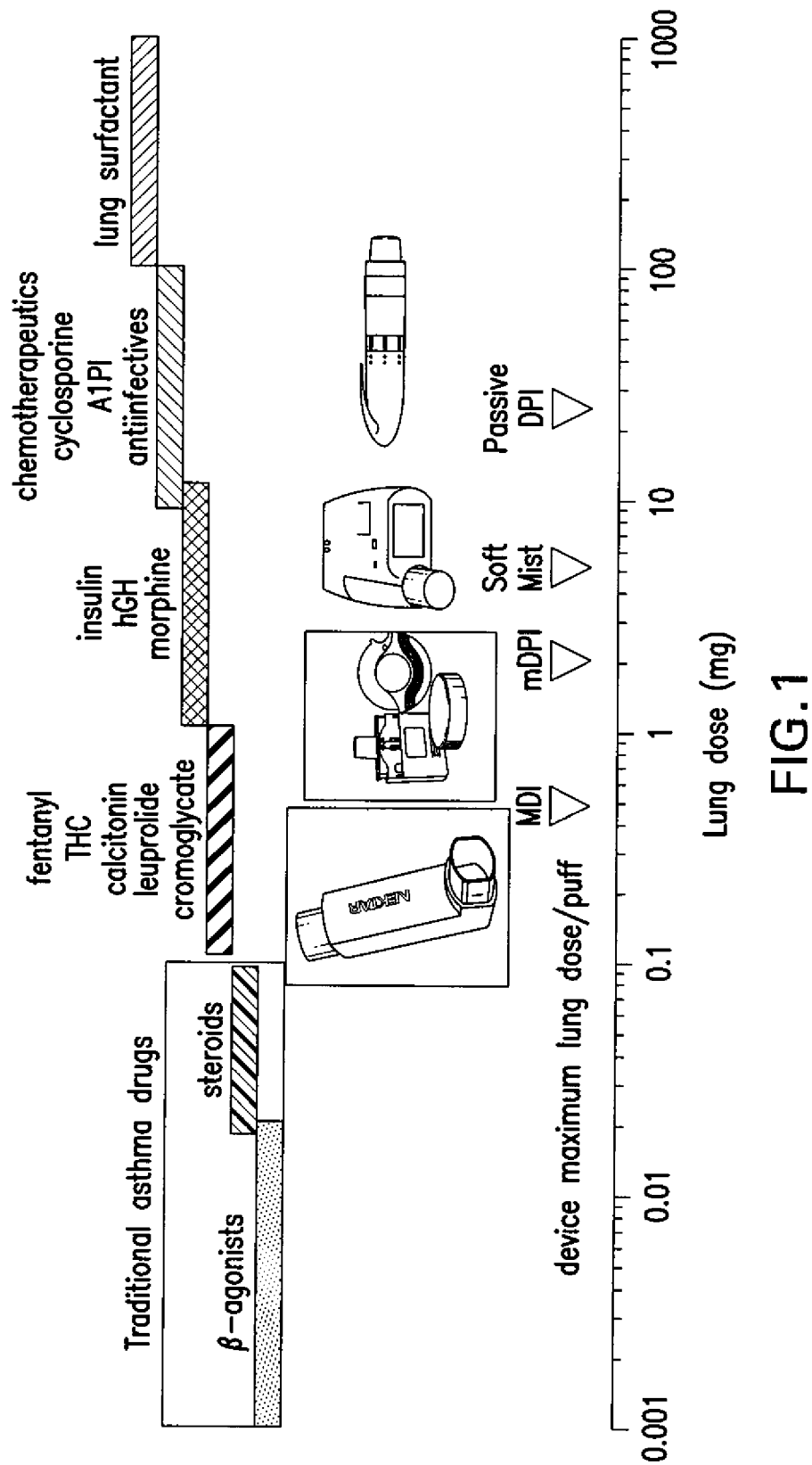

FIG. 6 compares the dispersibility of micronized ciprofloxacin betaine and spray-dried ciprofloxacin betaine inhalation powder according to the present invention, CIP. Powder dispersibility is quantitated by measuring the median diameter of the particles as a function of the driving pressure in the RODOS disperser attached to the Sympatec laser diffraction sizing instrument. CIP disperses to primary particles at much lower driving pressures than micronized drug, reflecting the reductions in interparticle cohesive forces afforded by the porous coating of phospholipid.

FIG. 7 is a plot demonstrating the improved lung targeting enabled by inhalation of ciprofloxacin betaine inhalation powder according to the present invention. The left panel compares differences in plasma $C_{max}$ for oral administration (PO) of 500 mg BID Cipro versus 32.5 mg QD of ciprofloxacin betaine inhalation powder according to the present invention, CIP by inhalation (IH). The middle panel presents the corresponding sputum levels. Finally, the right panel presents the improved targeting afforded by inhalation, as represented by the ratio of the sputum AUC to the Plasma AUC. Inhalation of ciprofloxacin leads to significantly higher sputum concentrations with correspondingly low systemic levels of drug. Lung targeting is improved 250-fold for the inhaled drug.

FIG. 8A through 8E are schematic sectional side views showing the operation of a dry powder inhaler that may be used to aerosolize a pharmaceutical formulation according to the invention.

DESCRIPTION

Definitions

It is to be understood that unless otherwise indicated the present invention is not limited to specific formulation components, drug delivery systems, manufacturing techniques, administration steps, or the like, as such may vary. Unless otherwise stated, a reference to a compound or component includes the compound or component by itself, as well as the compound in combination with other compounds or components, such as mixtures of compounds.

Before further discussion, a definition of the following terms will aid in the understanding of embodiments of the present invention.

As used herein, the singular forms "a," "an," and "the" include the plural reference unless the context clearly dictates otherwise. Thus, for example, reference to "a phospholipid" includes a single phospholipid as well as two or more phospholipids in combination or admixture unless the context clearly dictates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Reference herein to "one embodiment", "one version" or "one aspect" shall include one or more such embodiments, versions or aspects, unless otherwise clear from the context.

As used herein, the terms "treating" and "treatment" refer to reduction in severity and/or frequency of symptoms, elimination of symptoms and/or underlying cause, reduction in likelihood of the occurrence of symptoms and/or underlying cause, and improvement or remediation of damage. Thus, "treating" a patient with an active agent as provided herein includes prevention of a particular condition, disease or disorder in a susceptible individual as well as treatment of a clinically symptomatic individual.

As used herein, "therapeutically effective amount" refers to an amount that is effective to achieve the desired therapeutic result. A therapeutically effective amount of a given active agent will typically vary with respect to factors such as the type and severity of the disorder or disease being treated and the age, gender, and weight of the patient.

As used herein, the term "respiratory infections" includes, but is not limited to lower respiratory tract infections such as bronchiectasis (both the cystic fibrosis and non-cystic fibrosis indications), bronchitis (both acute bronchitis and acute exacerbation of chronic bronchitis), and pneumonia (including various types of complications that arise from viral and bacterial infections including hospital-acquired and community-acquired infections).

As used herein, "bulk density" refers to the bulk density measured by uniaxial compaction at a pressure of about 100,000 psi. This pressure corresponds to the pressure utilized during autofilling of powder into receptacles, such as capsules.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. Typically, powder samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 4 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, the relative dispersibility of spray-dried powders is determined with the Sympatec (laser diffraction) by varying the dispersing pressure of the RODOS dispersion unit, from about 0.2 bar to 4.0 bar. As used herein, the dispersibility index, $\delta$ (delta), is defined as the ratio of the $x_{50}$ measured at a dispersing pressure of 0.2 bar to that at 4.0 bar. A value of $\delta=1$ would be indicative of a powder which disperses readily at low dispersing pressures, while values less than 1 are indicative of incomplete powder dispersion at low dispersing pressures.

As used herein, specific surface area (SSA) refers to the SSA calculated from gas adsorption data according to a theory developed by Brunauer, Emmett, and Teller (*J Amer Chem Soc* 1938, 60:309), generally referred to as the BET method.

As used herein, particle porosity refers to the total pore volume in %, calculated from nitrogen gas absorption data. In nitrogen adsorption, the pores are filled (and emptied) according to the Kelvin capillary condensation equation. As the partial pressure of nitrogen increases, condensation of the gas will begin in the smaller pores and progressively fill larger and larger pores until bulk condensation occurs. Using this technique, nitrogen is first condensed in the pores by setting the partial pressure of nitrogen to a value near saturation. Then, the nitrogen is gradually desorbed in a stepwise fashion by reducing its vapor pressure. The pore size distribution is calculated by analyzing the nitrogen desorption isotherm using the Kelvin equation to determine the amount of condensed nitrogen in the pores (assuming a cylindrical pore geometry), wherein the adsorptive loss at each step represents the core volume of pores emptied during that step. The calculation is automated, and follows the algorithm proposed by Barrett et al (Barrett E P, Joyner L G, Halenda P P: The determination of pore volume and area distributions in porous substances I. computations from nitrogen isotherms. *J Amer Chem Soc* 1951, 73:373-380). This approach holds for pore diameters as small as about 2 nm, i.e., down to the micropore region.

Rugosity ($S_v$) is a measure of the surface roughness of an engineered powder. For the purposes of this invention, rugosity is calculated from the specific surface area obtained from BET measurements, the true density obtained by helium pycnometry, and the surface/volume ratio of the particle obtained by laser diffraction (Sympatec), viz:

$$\text{Rugosity}(S_v) = \frac{BET \cdot \rho_{true}}{S_v},$$

where $S_v = 6/D_{32}$.

As used herein, "mass median aerodynamic diameter" or "MMAD" refers to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. MMAD is determined herein by cascade impaction, unless the context indicates otherwise.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., the mass of the powder delivered, the emitted mass, to the mass of powder per unit dose placed into a suitable inhaler device prior to firing). The ED is an experimentally determined amount, and may be determined using an in vitro device set up which mimics patient dosing. To determine an ED value, as used herein, a nominal dose of dry powder (as defined herein) is placed into a suitable inhaler device, for example, a Turbospin® DPI device (PH&T, Italy), described in U.S. Pat. Nos. 4,069,819 and 4,995,385, which are incorporated herein by reference in their entireties. The inhaler device is actuated, dispersing the powder. The resulting aerosol cloud is then drawn from the device by vacuum (60 L/min) for 2 seconds after actuation, where it is captured on a tared glass fiber filter (Gelman, 47 mm diameter) attached to the device mouthpiece. The amount of powder that reaches the filter constitutes the delivered dose. For example, for a capsule containing 5 mg of dry powder that is placed into an inhalation device, if dispersion of the powder results in the recovery of 4 mg of powder on a tared filter as described above, then the ED for the dry powder composition is 80% [4 mg (delivered dose)/5 mg (nominal dose)].

As used herein, "effective amount" refers to an amount covering both therapeutically effective amounts and prophylactically effective amounts.

As used herein, "passive dry powder inhaler" refers to an inhalation device that relies upon a patient's inspiratory effort to fluidize and disperse a pharmaceutical composition contained within the device in a reservoir or in a unit dose form.

As used herein, "active dry powder inhaler" refers to inhaler devices that comprise a means for providing energy to fluidize and disperse the drug composition, such as pressurized gas, and/or vibrating or rotating elements.

The entire contents and disclosure of each reference referred to herein, including any and all US and PCT (or ex-US) patents and US and PCT (or ex-US) patent application publications, is hereby incorporated herein by reference for all purposes.

DESCRIPTION OF THE INVENTION

The present invention relates to the pulmonary delivery of an effective dose of an active agent to the lungs for the treatment of lung infections.

In one or more embodiments herein, the active agent drug substance is selected from the family of quinolone and quinolone-like drugs (including fluoroquinolones), such as, naladixic acid, cinoxacin, norfloxacin, ciprofloxacin, ofloxicin, enoxacin, moxifloxacin, levofloxacin, and pefloxacin, to name a few. In one particular version, due to its outstanding activity against *P. aeruginosa*, formulations and compositions comprise ciprofloxacin.

In one or more embodiments of the present invention, the lung residence time is not controlled by encapsulation in a carrier system (e.g., liposomes or polymeric carriers), rather the lung residence time (as well as pulmonary delivery to the appropriate sites) is mediated by formulations comprising fluoroquinolone betaine suitable for inhalation as described herein. One or more embodiments of the present invention thus comprise a fluoroquinolone betaine, such as ciprofloxacin betaine, for inhalation, and result in a lung half-life of greater than 3 hr, with concomitant improved efficacy against *P. aeruginosa* relative to soluble forms of fluoroquinolone, such as ciprofloxacin hydrochloride.

In general, bacteria causing respiratory tract infections (RTIs) like bronchitis, acute exacerbations of chronic bronchitis (AECB), and CF reside within the lumen of the airways, at the mucosal cell surface and within the bronchial mucosal tissue. In pneumonia, bacteria are found mainly in alveolar locations. In order to reach their targets, i.e., the causative pathogens, orally or intravenously administered antibacterial agents have to penetrate the alveolar space; the agents must cross the alveolar membrane, which is relatively impermeable, and have to distribute in the epithelial lining fluid (ELF) covering the mucosal cell surface. Thus, concentrations of antibacterial agents in the ELF/sputum can be considered as a clinically relevant indicator for target site concentrations. Hence, it is an object of the present invention to provide formulations for inhalation which provide inhaled lung doses of from 10-30 mg in as few puffs (e.g. a single inhalation) as possible. In one or more embodiments comprising a formulation/device combination having a lung delivery efficiency of between 20% and 60% w/w, this corresponds to a nominal dose in the range from 15 mg to 150 mg or 0.3 mg/kg to 3.0 mg/kg for a 50 kg young adult.

One or more embodiments of formulations of the present invention can achieve high concentrations at the site of the infection to overcome high MIC values of *P. aeruginosa*. Thus the pharmacokinetics as prerequisite to influence *P. aeruginosa* growth and reduce *P. aeruginosa* virulence should have an impact on FEV1 as a pharmacodynamic correlate. Moreover, the formulations of the present invention can reduce incidence and severity of acute exacerbations and improve the quality of life of CF patients by dramatically reducing the administration time of the drug.

The present invention offers additional advantages. For example, as noted above, most other aerosolized therapeutics require significantly higher lung doses, whether delivered for local lung disease, or systemic applications. The delivery of large lung doses (>10 mg) has traditionally been accomplished by jet nebulization, as standard formulation and device technologies used in asthma therapy (e.g., metered dose inhalers and multidose dry powder inhalers), are not effective in delivering doses of this magnitude. As discussed, *P. aeruginosa* infections in cystic fibrosis (CF) patients (lung dose≈30 mg) are currently treated via jet nebulization of aqueous solutions of the aminoglycoside tobramycin (TOBI®, Novartis, Emeryville, Calif.) with a PARI LC Plus® nebulizer. The long administration times and lack of portability of jet nebulizers and the large number of inhalation treatments have been observed to negatively impact the quality of life of CF patients. As a result, physicians are faced with treatment compliance challenges. Due to the demanding nature of the treatment programs, any time savings in treatment is viewed as a huge driver for improving patient compliance and quality of life. The ability to utilize a portable inhaler that can be carried in a shirt pocket or purse is also a huge advantage, as the patient is no longer tied to a bulky compressor requiring electrical power. Hence, the patient can go hiking or enjoy some other outdoor activity and still be able to administer their medication.

As discussed above, the residence time for water soluble fluoroquinolones, such as ciprofloxacin hydrochloride, in the lungs is very short (half-life of about 0.2 hr) (Wong et al: In: "Liposomes in biomedical applications (A T Florence, G Gregoriadis, eds) Harwood Academic Press, Amsterdam, 1995, pp 105-120). Thus, in one version of the present invention, a composition is formulated so that the fluoroquinolone, such as ciprofloxacin, is delivered to the lungs as has a half life that is at least 0.3 hours. Even more preferably, the half life is significantly longer, such as at least 1.5 hours, more preferably at least 3 hours, and more preferably at least 6 hours.

In contrast to the short half-life of soluble ciprofloxacin, the half-life of the zwitterionic form found near neutral pH, ciprofloxacin betaine, is significantly longer (Endermann R, Labischinski H, Ladel C et al: treatment of bacterial diseases of the respiratory organs. US Patent Appl 2004/0254194 A1).

One or more embodiments of the present invention thus comprise dry powder formulations of ciprofloxacin betaine for inhalation. Embodiments of ciprofloxacin betaine (and other fluoroquinolones) and methods of treatment using such compounds are described in US Patent Application Publication 2004/0254194, the entire disclosure of which is incorporated by reference herein. Formulations comprising the betaine forms of other fluoroquinolones (e.g., levofloxacin, moxifloxacin) may be utilized in the present invention in place of or in addition to the ciprofloxacin betaine. Ciprofloxacin betaine has very low water solubility (See FIG. 2). One or more embodiments of the present invention thus comprise ciprofloxacin betaine formulated as micronized crystals coated with a porous layer of a hydrophobic excipient, preferably a porous layer of a phospholipid. Ciprofloxacin betaine is formed at pH values in the range from 6.0 to 8.8. pH values near neutral are preferred.

In one or more embodiments, at least 50% of the ciprofloxacin betaine crystal particulates have a mass median diameter ($x_{50}$) less than about 5 microns, more preferably less than about 3 microns, and even more preferably less than about 2 microns. In one or more embodiments, at least 90% of the ciprofloxacin betaine crystal particulates have a mass median diameter ($x_{90}$) less than 10 microns, more preferably less than 7 microns, and even more preferably less than 5 microns. The MMAD of the resulting powder particles is dependent on the starting particulate size of the ciprofloxacin betaine crystals. The smaller the MMD of the crystal, the smaller the MMAD of the resulting ciprofloxacin betaine containing powder particles.

In one or more embodiments, larger ciprofloxacin betaine crystals may be micronized to the desired size by standard top-down methods including, but not limited to, jet-milling and wet-milling (high pressure homogenization).

Alternatively or additionally, micronization may be completed by bottom-up processing methods in which the drug is dissolved in a solution and then precipitated. These include methods such as spray-drying and spray freeze-drying. Other suitable size reduction processes are known in the art and include, without limitation, supercritical fluid processing methods such as those disclosed in WO 95/01221, WO 96/00610, and WO 98/36825, cryogenic milling, wet milling, ultrasound, high pressure homogenization, microfluidization, crystallization processes, as well as the processes disclosed in U.S. Pat. No. 5,858,410, all of which are hereby incorporated in their entirety by reference.

Compositions of the present invention comprising the fluorquinolone betaine, such as ciprofloxacin betaine, may include various amounts of the active agent. For example, the amount of fluoroquinolone betaine, such as ciprofloxacin betaine, may comprise at least about 30% w/w, 40% w/w, 50% w/w, 60% w/w, 70% w/w, 80% w/w, or 90% w/w. In some embodiments the desired powder fluidization and dispersibility are obtained when the fluoroquinolone betaine, such as ciprofloxacin betaine, is present in the composition at from about 50% w/w to 70%.

One or more embodiments of the invention comprise a pharmaceutical composition or formulation comprising a fluoroquinolone betaine, such as ciprofloxacin betaine, and, optionally, one or more pharmaceutically acceptable excipients.

In one or more embodiments, the pharmaceutically acceptable excipient comprises one or more at least partially hydrophobic excipients. For example, the hydrophobic excipients may comprise one or more of lipids, long-chain fatty acid soaps (e.g., magnesium stearate, potassium stearate), hydrophobic amino acids or peptides (e.g., leucine, trileucine), and cholesterol.

In one or more embodiments, the pharmaceutically acceptable excipients comprise a lipid, such as a phospholipid. In one version, a phospholipid matrix is formed. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; and 6,503,480, and in co-pending and co-owned U.S. application Ser. No. 10/750,934, filed on Dec. 31, 2003, all of which are incorporated herein by reference in their entireties.

In one or more embodiments, excipients are present as a porous rugous coating on the active agent. When selected and formulated in such a manner, the excipients provide improvements in powder fluidization and dispersibility, relative to "smooth" coatings of low porosity or rugosity.

Phospholipids from both natural and synthetic sources may be used in varying amounts. When phospholipids are present, the amount is typically sufficient to coat the active agent(s) with an amount sufficient to provide a porous coating of phospholipid. When present, the phospholipid content generally ranges from about 10 wt % to about 70 wt %, such as about 30 wt % to about 50 wt %.

Generally, compatible phospholipids comprise those that have a gel to liquid crystal phase transition greater than about 40° C., such as greater than about 60° C., or greater than about 80° C. The incorporated phospholipids may be relatively long chain (e.g., $C_{16}$-$C_{22}$) saturated lipids. Exemplary phospholipids useful in the disclosed stabilized preparations include, but are not limited to, phosphatidylcholines such as dipalmitoylphosphatidylcholine, and distearoylphosphatidylcholine, and hydrogenated egg or soy phosphatidylcholine (e.g., E-100-3, S-100-3, available from Lipoid KG, Ludwigshafen, Germany). Natural phospholipids are preferably hydrogenated with a low iodine value (<10).

The phospholipids may optionally be combined with a divalent metal ion. Such a divalent metal ion acts to decrease phospholipid headgroup hydration, thereby increasing the phospholipid gel to liquid crystal phase transition, and the wettability of the powders on lung lining fluid.

Examples of metal ions include, but are not limited to, divalent cations, including calcium, magnesium, zinc, and the like. For instance, when phospholipids are used, the pharmaceutical composition may also comprise a polyvalent cation, as disclosed in WO 01/85136 and WO 01/85137, which are incorporated herein by reference in their entireties. The polyvalent cation may be present in an amount effective to increase the melting temperature ($T_m$) of the phospholipid such that the pharmaceutical composition exhibits a $T_m$ which is greater than about 60° C., preferably greater than about 80° C., or greater than about 100° C. The molar ratio of polyvalent cation to phospholipid may be at least about 0.05:1, such as about 0.05:1 to about 0.5:1. In one or more embodiments, a molar ratio of polyvalent cation:phospholipid is about 0.5:1. It is believed that the divalent metal ion binds to the phosphate groups on the zwitterionic phosphatidylcholine headgroup, displacing water molecules in the process. Molar ratios of metal ion to phospholipid in excess of 0.5 may result in free metal ion not bound to the phosphate groups. This can significantly increase the hygroscopicity of the resulting dry powder. When the polyvalent cation is calcium, it may be in the form of calcium chloride. Although metal ions, such as calcium, are often included with phospholipid, none is required, and can be problematic when other ions are present in the formulation (e.g., phosphate, which may precipitate the calcium ions as calcium phosphate).

One or more embodiments of a composition of the present invention, the excipient may additionally or alternatively include additives to further enhance stability or biocompatibility of the formulation. For example, various salts, buffers, chelators, and taste masking agents are contemplated. The use of these additives will be understood to those of ordinary skill in the art and the specific quantities, ratios and types of agents can be determined empirically without undue experimentation.

One or more embodiments of a composition of the present invention, the excipient may additionally or alternatively include excipients which perform similar and/or alternative functions. For example, the composition may include targeting excipients to enhance the targeting of particles to specific cells (e.g., pulmonary macrophages). In one version of the invention, the pharmaceutical formulation may comprise one or more targeting agents. For example, the pharmaceutical formulation may comprise a targeting agent that directs the particles and/or active agent to cellular targets, such as pulmonary macrophages. This is particularly useful when the pharmaceutical formulation is being administered to treat an infectious disease where a pathogen is taken up by pulmonary macrophages. Such infectious diseases are difficult to treat with conventional systemic treatment with anti-infective active agents. However, by incorporating a targeting agent, the particle may be more readily taken up by the pulmonary macrophage and more effectively delivered to the site of infection. This method of treatment is particularly effective for the treatment of tuberculosis, big-warfare agents, such as anthrax, and some types of cancer. The targeting agents may comprises, for example, one or more of phosphatidylserine, hIgG, and muramyl dipeptide, as described in PCT publications WO 99/06855, WO 01/64254, WO 02/09674, and WO 02/87542 and in U.S. Pat. No. 6,630,169, all of which are incorporated herein by reference in their entireties. The targeting process can be more effective if the active agent remains in the lungs for a long period of time. Accordingly, in one version, the pharmaceutical formulation comprises a targeting agent and sufficient amounts of the lipid component to ensure that the active agent is maintained in the lung for a predetermined period of time useful to treat an infectious disease where a pathogen is taken up by pulmonary macrophages. Particularly when the pharmaceutical formulation comprises such a targeting agent, the particle size is preferably less than 6 microns because larger particles are not readily taken up by pulmonary macrophages.

In one or more embodiments of the composition of the present invention, the excipient may additionally or alternatively include the pegylated phosphatidylethanolamines, such as $PEG_{2000}$-PE and/or $PEG_{5000}$-PE (where the number refers to the molecular weight of the PEG unit), to further increase lung residence time by avoiding clearance by macrophages and/or to facilitate penetration of the composition particles into the mucus or sputum layer lining the pulmonary epithelium. For particles less than 1 μm in geometric size it may also be possible to penetrate into *Pseudomonas aeruginosa* biofilms.

Figure 3:
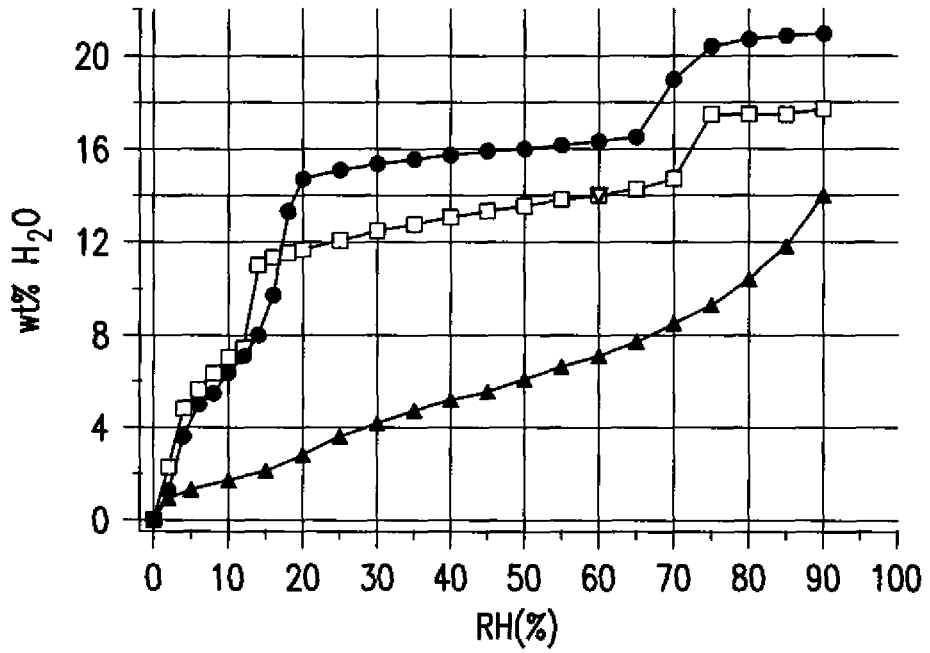
FIG. 3 is a plot of the equilibrium water vapor sorption isotherms (T=25° C.) of ciprofloxacin betaine drug substance (closed circles), ciprofloxacin betaine inhalation powder according to the present invention, CIP (closed squares), and placebo powder (closed triangles). Also shown is a single point (inverted triangle) measured by Karl Fischer titrimetry at RH=60% for CIP.

Ciprofloxacin betaine may be formulated as a variety of polymorphs and/or hydrates. In one or more embodiments the ciprofloxacin betaine comprises a 3.5 hydrate, which has been found to possess excellent chemical and physical stability under the conditions utilized in the present invention. In one or more embodiments, the ciprofloxacin betaine in the composition consists essentially of the 3.5 hydrate form. As shown in FIG. 3, the 3.5 hydrate is found at water contents in spray-dried powders between about 10% w/w and 15% w/w. Other polymorphs or hydrates or mixtures of ciprofloxacin betaine may alternatively or additionally be utilized as well, but under the present conditions, the 3.5 hydrate is preferred. It has been discovered that polymorphic ciprofloxacin betaine is converted to a single polymorphic form, the 3.5 hydrate, when spray-dried using the emulsion-based spray-drying process described herein. This occurs despite the fact that the crystals remain insoluble throughout the manufacturing process. Other processing methods generally produce a mixture of hydrates.

In one or more versions, a composition for pulmonary administration comprises discrete particles that each comprise a flouroquinolone and an excipient. The fluoroquinolone is in a form whereby it has a half-life in the lungs of at least 1.5 hours. For example, the fluoroquinolone may comprise a fluoroquinolone betaine such as ciprofloxacin betaine. According to this version, the particles have a mass median aerodynamic diameter from about 1 μm to about 5 μm and a bulk density of less than about $1.0 g/cm^3$, more preferably less than about $0.6 g/cm^3$, and more preferably in the range of from about $0.2 g/cm^3$ to about $0.5 g/cm^3$.

In one or more versions, the fluoroquinolone betaine, such as ciprofloxacin betaine, is incorporated in an excipient matrix that forms a discrete particle, and the pharmaceutical composition comprises a plurality of the discrete particles. The discrete particles may be sized so that they are effectively administered and/or so that they are available where needed. For example, for an aerosolizable pharmaceutical composition, the particles are of a size that allows the particles to be aerosolized and delivered to a user's respiratory tract during the user's inhalation.

In some versions, the pharmaceutical composition comprises particles having a mass median diameter less than about 10 μm, such as less than about 5 μm, less than about 3 μm, or less than about 1 μm, and may be from 1 μm to 10 μm, such as from about 1 μm to 5 μm. In one or more embodiments a mass median diameter of the powder is between about 1 and 3 μm.

In one or more embodiments a bulk density of the spray-dried powder is about $1.0 g/cm^3$, and more preferably less than about $0.6 g/cm^3$ and more preferably from $0.2 g/cm^3$ to $0.6 g/cm^3$.

In one or more embodiments a pH of the powder on reconstitution is between 6.0 and 8.8. In one or more embodiments, the pH is such as to provide the crystalline ciprofloxacin betaine upon reconstitution.

In one or more embodiments a moisture content of a powder is between about 10% and 15% w/w. In one or more embodiments, a moisture content of a spray-dried powder is such as to provide the crystalline ciprofloxacin betaine 3.5 hydrate polymorph.

In one or more embodiments, a specific surface area of the powder is between 8 $m^2/g$ and 20 $m^2/g$. In one or more embodiments a porosity is between about 5% and 20%. In one or more embodiments a rugosity ($S_v$) is between 3 and 10. In one or more embodiments, a powder of the present invention comprises at least two of the specific surface area, porosity and rugosity measurements defined herein. In one or more embodiments, a powder of the present invention comprises at least three of the specific surface area, porosity and rugosity measurements defined herein.

In one or more embodiments, a powder of the present invention comprises a mass median aerodynamic diameter from about 1 μm to about 5 μm, such as about 1.5 μm to about 4 μm, or about 2 μm to about 4 μm. In general, if the particles are too large, fewer particles will reach the deep lung. If the particles are too small, a larger percentage of the particles may be exhaled. In order to achieve the desired lung dose of greater than 10 mg in the desired number of inhalations, it is preferred that a fine particle dose less than 4.7 microns be greater than 10 mg, more preferably greater than 16 mg and more preferably greater than 20 mg.

In one or more embodiments of the present invention, an emulsion-based spray-drying process is used to create fluoroquinolone betaine crystals coated with a porous layer of a hydrophobic excipient. The resulting particles may be administered in a high dose to a CF patient in need thereof, with a minimum number of inhalations, such as fewer than four, preferably fewer than three, more preferably fewer than two, and most preferably one.

In one or more embodiments, the compositions of the present invention are powders comprising discrete particles.

In one or more embodiments, the powders are prepared by a solvent removal process. While several procedures are generally compatible with the present invention, particularly preferred embodiments typically comprise perforated microstructures or porous particles formed by spray drying or freeze drying. As is well known, spray drying is a process that converts a liquid feedstock to dried powder particles. With respect to pharmaceutical applications, it will be appreciated that spray drying has been used to provide powdered material for various administrative routes including inhalation.

In one or more embodiments, the powder compositions of the present invention are prepared by spray-drying. In an exemplary embodiment, a feedstock comprises a fluoroquinolone betaine. For example, in one version, the feedstock comprises micronized crystals of a fluoroquinolone betaine, such as ciprofloxacin betaine, dispersed in the continuous phase of an oil-in-water emulsion. The feedstock may also comprise a hydrophobic excipient, such as a phospholipid. The dispersed phase in the submicron emulsion droplets may or may not also comprise a fluorocarbon. In one or more embodiments, the fluorocarbon is selected from the group comprising perfluorooctyl bromide, perfluorodecalin, perfluorooctyl ethane, and mixtures thereof. In one or more embodiments, the fluorocarbon is stabilized by a monolayer of the phospholipid excipient. During spray-drying the emulsion droplets aid in the formation of a porous coating of phospholipid on the surface of the betaine crystals. The concentration of active agent and optional active agents depends on the amount of agent required in the final powder and the type of inhaler to be employed. In one or more embodiments, such concentrations may be as described previously. The volume fraction of fluorocarbon in the feedstock, if used, may be in the range from 3% to 50% w/v, preferably about 5% to 30% w/v. Examples of spray drying particles comprising lipid coated crystals can also be found in WO 2004/060351, in U.S. Pat. No. 7,326,691, and in US Patent Application 2006/0165606, all of which are incorporated herein by reference in their entireties.

In one or more embodiments, the feedstock may comprise a blowing agent. The blowing agent is preferably a fluorinated compound (e.g. perfluorohexane, perfluorooctyl bromide, perfluorodecalin, perfluorobutyl ethane) which vaporizes during the spray-drying process, leaving behind generally porous particles, such as betaine crystals with a porous DSPC coat which are aerodynamically light. As will be discussed in more detail below, other suitable liquid blowing agents include nonfluorinated oils, chloroform, Freons, ethyl acetate, alcohols and hydrocarbons. Nitrogen and carbon dioxide gases are also contemplated as a suitable blowing agent.

Although the perforated microstructures may preferably formed using a blowing agent as described above, it will be appreciated that, in some instances, no additional blowing agent is required and an aqueous dispersion of the medicament and/or excipients and surfactant(s) are spray dried directly. In such cases, the formulation may be amenable to process conditions (e.g., elevated temperatures) that may lead to the formation of relatively porous microparticles.

Regardless of which, if any, blowing agent is ultimately selected, it has been found that compatible perforated microstructures may be produced particularly efficiently using a Buchi mini spray drier (model B-191, Switzerland). As will be appreciated by those skilled in the art, the inlet temperature and the outlet temperature of the spray drier are selected to be of such a level to provide the desired particle size and to result in a product that has the desired activity of the medicament. In this regard, the inlet and outlet temperatures are adjusted depending on the melting characteristics of the formulation components and the composition of the feed stock. Commercially available spray dryers are well known to those in the art, and suitable settings for any particular dispersion can be readily determined through standard empirical testing, with due reference to the examples that follow.

Particularly preferred embodiments of the present invention comprise spray drying preparations comprising a surfactant such as a phospholipid and a ciprofloxacin betaine active agent. In other embodiments the spray drying preparation may further comprise an excipient comprising a hydrophilic moiety such as, for example, a carbohydrate (i.e. glucose, lactose, or starch) in addition to any selected surfactant. In this regard various starches and derivatized starches suitable for use in the present invention. Other optional components may include conventional viscosity modifiers, buffers such as phosphate buffers or other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

When phospholipids are utilized as the matrix material, it is preferable to further incorporate a polyvalent cation into the feedstock, as disclosed in PCT WO 01/85136 and WO 01/85137, hereby incorporated in their entirety by reference. Suitable polyvalent cations are preferably a divalent cation including calcium, magnesium, zinc, iron, and the like. The polyvalent cation is present in an amount effective to increase the $T_m$ of the phospholipid such that the particulate composition exhibits a $T_m$ which is greater than its storage temperature $T_s$ by at least 20° C., preferably at least 40° C.

Whatever components are selected, an initial step in particulate production typically comprises feed stock preparation. Preferably the selected drug is dissolved in water to produce a concentrated solution. For insoluble crystalline active agents, as will typically be the case in the present invention, the drug may be dispersed directly in the emulsion. The concentration of the active or bioactive agent used is dependent on the amount of agent required in the final powder and the performance of the delivery device employed (e.g., the fine particle dose for a MDI or DPI). As needed, additional excipients, such as those listed above, may also be added to the feedstock.

In selected embodiments an oil-in-water emulsion is then formed in a separate vessel. The oil employed is preferably a fluorocarbon (e.g., perfluorooctyl bromide, perfluorodecalin) which is emulsified using a surfactant such as a long chain saturated phospholipid. For example, one gram of phospholipid may be homogenized in 150 g hot distilled water (e.g., 60.degree. C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting perfluorocarbon in water emulsion is then processed using a high pressure homogenizer to reduce the particle size. Typically the emulsion is processed at 12,000 to 18,000 psi, 5 discrete passes and kept at 50 to 80.degree. C.

In any event, operating conditions such as inlet and outlet temperature, feed rate, atomization pressure, flow rate of the drying air, and nozzle configuration can be adjusted in accordance with the manufacturer's guidelines in order to produce the required particle size, and production yield of the resulting dry microstructures. Exemplary settings are as follows: an air inlet temperature between 60.degree. C. and 170.degree. C.; an air outlet between 40.degree. C. to 120.degree. C.; a feed rate between 3 ml to about 15 ml per minute; and an aspiration air flow of 300 L/min. and an atomization air flow rate between 25 to 50 L/min. The selection of appropriate apparatus and processing conditions are well within the purview of a skilled artisan in view of the teachings herein and may be accomplished without undue experimentation. In any event, the use of these and substantially equivalent methods provide for the formation of porous aerodynamically light microspheres with particle diameters appropriate for aerosol deposition into the lung, microstructures that are porous, almost honeycombed or foam-like in appearance. In especially preferred embodiments the perforated microstructures comprise porous spray dried particles. The solids content in the spray-drying feedstock will typically be in the range from 0.5 wt % to 10 wt %, such as 1.0 wt % to 5.0 wt %. The settings will, of course, vary depending on the type of equipment used. In any event, the use of these and similar methods allow formation of coated crystals with diameters appropriate for aerosol deposition into the lung. One key aspect is that the outlet temperature and collector temperature on the dryer must be maintained at temperatures less than the $T_m$ of the resulting formulation.

The emulsion-based feedstock may be prepared by first dispersing the polyvalent cation and phospholipid in hot distilled water (e.g., 70° C.) using a suitable high shear mechanical mixer (e.g., Ultra-Turrax model T-25 mixer). Typical process conditions might be mixing at 8000 rpm for 2 to 5 min. A fluorocarbon is then added dropwise to the dispersed surfactant solution while mixing. The resulting fluorocarbon-in-water emulsion may then be processed using a high pressure homogenizer to reduce the particle size. Typically, the emulsion is processed for five discrete passes at 8,000 to 20,000 psi to produce droplets with a median diameter less than 600 nm. Micronized ciprofloxacin betaine is then added into the continuous phase of the emulsion and mixed and/or homogenized.

In one version, the pharmaceutical formulation is composed of porous microstructures having a bulk density less than 1.0 g/cm³, more preferably less than 0.5 g/cm³, more preferably less than 0.3 g/cm³, and sometimes less 0.1 g/cm³. In one particular version, the bulk density of the powder is from 0.2 g/cm³ to 0.6 g/cm³. By providing particles with very low bulk density, the minimum powder mass that can be filled into a unit dose container is reduced, which reduces and often eliminates the need for carrier particles. That is, the relatively low density of the powders of the present invention provides for the reproducible administration of relatively low dose pharmaceutical compounds. Moreover, the elimination of carrier particles will potentially minimize throat deposition and any "gag" effect, since the large lactose carrier particles typically used in the art will impact the throat and upper airways due to their size. With the present invention, the need for these large particles can be avoided.

In one or more embodiments, a powder formulation according to the invention comprises from about 50% to about 70%, more preferably about 65% w/w active agent, such as a fluoroquinolone, from about 15% to about 35%, more preferably about 20% w/w hydrophobic excipient such as a phospholipid, from about 1% to about 3%, more preferably about 2% w/w of a metal cation containing material, from about 10% to about 15%, more preferably about 12% w/w water. In one particular version, a powder formulation of the invention comprises from about 50% to about 70%, more preferably about 65% w/w ciprofloxacin betaine, preferably the 3.5 hydrate, from about 15% to about 35%, more preferably about 20% w/w distearoylphosphatidylcholine, and from about 1% to about 3%, more preferably about 2% w/w calcium chloride dihydrate, from about 10% to about 15%, more preferably about 12% w/w water, and <1% w/w residual perfluorooctyl bromide.

The powder pharmaceutical formulation may be administered using an aerosolization device. In a preferred version, the formulation is in powder form and is administered using a dry powder inhaler as described in U.S. patent application Ser. No. 09/888,311 filed on Jun. 22, 2001, in WO 02/83220, in U.S. Pat. No. 6,546,929, and in U.S. patent application Ser. No. 10/616,448 filed on Jul. 8, 2003. Alternatively, the aerosolization device may be a nebulizer, as described in WO 99/16420. All of these patents and patent applications are incorporated herein by reference in their entireties.

In one version, the powder composition is in dry powder form and is contained within a unit dose receptacle which may be inserted into or near the aerosolization device to aerosolize the unit dose of the composition. This version is useful in that the dry powder form may be stably stored in its unit dose receptacle for a long period of time. In addition, this version is convenient in that no refrigeration or external power source is required for aerosolization.

In some instances, it is desirable to deliver a unit dose, such as doses of 5 mg or greater, more preferably 10 mg or greater, and more preferably 16 mg or greater of active agent to the lung in a single inhalation. The above described phospholipid porous dry powder particles allow for doses of 5 mg or greater, 10 mg or greater, 16 mg or greater, 25 mg or greater, and 32 mg or greater to be delivered in a single inhalation and in an advantageous manner. Alternatively, the dose may be delivered in two, three or four inhalations. To achieve this, the bulk density of the powder is preferably less than 1.0 g/cm³, more preferably less than 0.6 g/cm³. Generally, a drug loading of more than 5%, more preferably more than 10%, more preferably more than 20%, more preferably more than 30%, and most preferably more than 40% is also desirable when the required lung dose in more than 5 mg. These unit dose pharmaceutical formulations may be contained in a capsule that may be inserted into an aerosolization device. The capsule may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose (HPMC), polyethyleneglycol-compounded HPMC, hydroxyproplycellulose, agar, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical formulation.

The sizes of capsules generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively, as shown in Table 1. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. No. 4,846,876, U.S. Pat. No. 6,357,490, and in the PCT application WO 00/07572 published on Feb. 17, 2000, all of which are incorporated herein by reference in their entireties.

In one version, the powder is loaded in size 2 capsules or smaller. Capsule sizes 2 and 3 are preferably employed, so as to maximize the dose that can be delivered while not exceeding the volume or mass of powder that can be emptied in a single inhalation by a pediatric CF patient.

TABLE 1

| Capsule sizes | | | | | | | |
|---|---|---|---|---|---|---|---|
| Capsule Size | | | | | | | |
| 000 | 00 | 0 | 1 | 2 | 3 | 4 | 5 |
| Volume (ml) 1.37 | 0.95 | 0.68 | 0.50 | 0.37 | 0.30 | 0.21 | 0.13 |

After filling, a top portion may be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

Figure 8A:
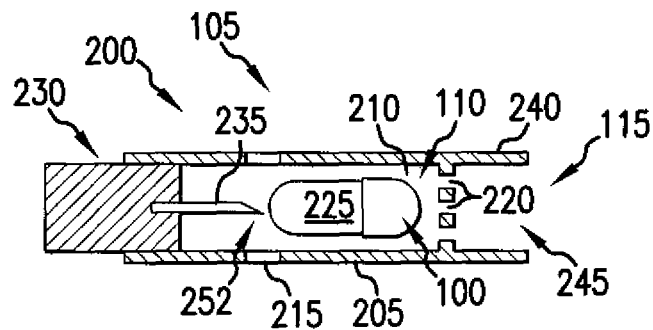

An example of a dry powder aerosolization apparatus particularly useful in aerosolizing a pharmaceutical formulation 100 according to the present invention is shown schematically in FIG. 8A. The aerosolization apparatus 200 comprises a housing 205 defining a chamber 210 having one or more air inlets 215 and one or more air outlets 220. The chamber 210 is sized to receive a capsule 225 which contains an aerosolizable pharmaceutical formulation. For example, the capsule may contain a composition comprising particles comprising a fluoroquinolone betaine, such as ciprofloxacin betaine. A puncturing mechanism 230 comprises a puncture member 235 that is moveable within the chamber 210. Near or adjacent the outlet 220 is an end section 240 that may be sized and shaped to be received in a user's mouth or nose so that the user may inhale through an opening 245 in the end section 240 that is in communication with the outlet 220.

The dry powder aerosolization apparatus 200 utilizes air flowing through the chamber 210 to aerosolize the pharmaceutical formulation in the capsule 225. For example, FIGS. 8A through 8E illustrate the operation of a version of an aerosolization apparatus 200 where air flowing through the inlet 215 is used to aerosolize the pharmaceutical formulation and the aerosolized pharmaceutical formulation flows through the outlet 220 so that it may be delivered to the user; through the opening 245 in the end section 240. The dry powder aerosolization apparatus 200 is shown in its initial condition in FIG. 8A. The capsule 225 is positioned within the chamber 210 and the pharmaceutical formulation is contained within the capsule 225.

Figure 8B:
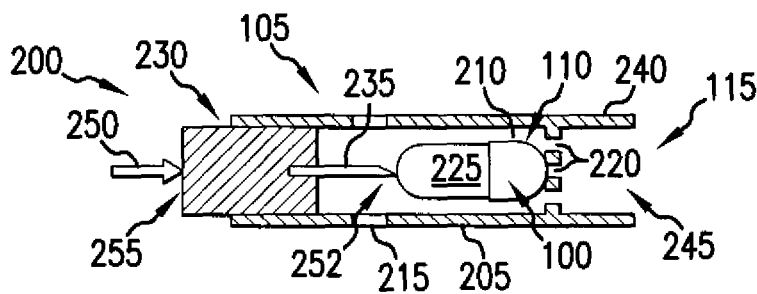

To use the aerosolization apparatus 200, the pharmaceutical formulation in the capsule 225 is exposed to allow it to be aerosolized. In the version of FIGS. 8A though 8E, the puncture mechanism 230 is advanced within the chamber 210 by applying a force 250 to the puncture mechanism 230. For example, a user may press against a surface 255 of the puncturing mechanism 230 to cause the puncturing mechanism 230 to slide within the housing 205 so that the puncture member 235 contacts the capsule 225 in the chamber 210, as shown in FIG. 8B.

Figure 8C:
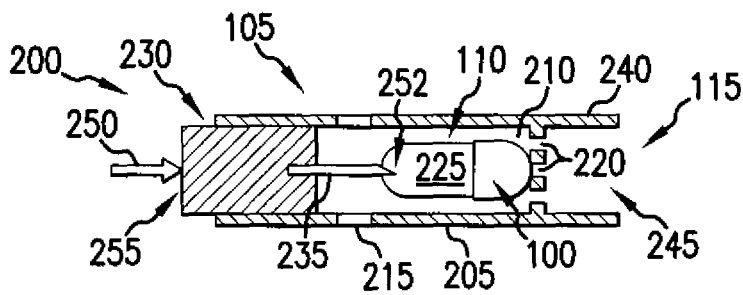
Figure 8D:
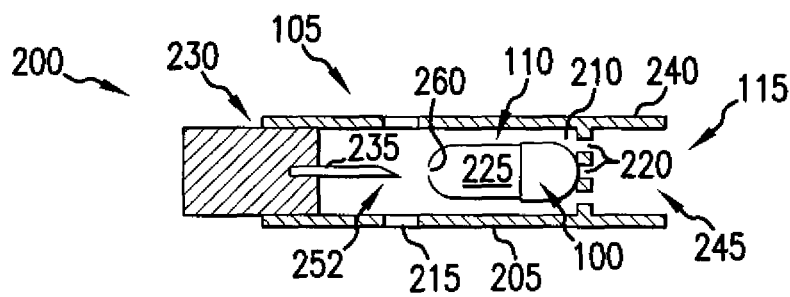
Figure 8E:
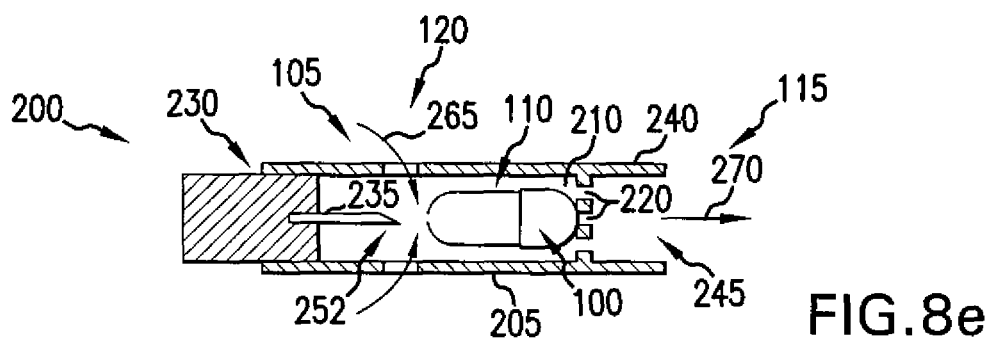

By continuing to apply the force 250, the puncture member 235 is advanced into and through the wall of the capsule 225, as shown in FIG. 8C. The puncture member may comprise one or more sharpened tips 252 to facilitate the advancement through the wall of the capsule 225. The puncturing mechanism 230 is then retracted to the position shown in FIG. 8D, leaving an opening 260 through the wall of the capsule 225 to expose the pharmaceutical formulation in the capsule 225. Air or other gas then flows through an inlet 215, as shown by arrows 265 in FIG. 8E. The flow of air causes the pharmaceutical formulation to be aerosolized.

When the user inhales 270 through the end section 240 the aerosolized pharmaceutical formulation is delivered to the user's respiratory tract. In one version, the air flow 265 may be caused by the user's inhalation 270. In another version, compressed air or other gas may be ejected into the inlet 215 to cause the aerosolizing air flow 265.

A specific version of a dry powder aerosolization apparatus 200 is described in U.S. Pat. No. 4,069,819, U.S. Pat. No. 4,995,385, U.S. application Ser. Nos. 10/298,177; 10/295,783; 10/821,652; 10/821,624; 10/822,850; 10/704,160; 10/714,511; and 10/313,419, all of which are incorporated herein by reference in their entireties. In such an arrangement, the chamber 210 comprises a longitudinal axis that lies generally in the inhalation direction, and the capsule 225 is insertable lengthwise into the chamber 210 so that the capsule's longitudinal axis may be parallel to the longitudinal axis of the chamber 210. The chamber 210 is sized to receive a capsule 225 containing a pharmaceutical formulation in a manner which allows the capsule to move within the chamber 210. The inlets 215 comprise a plurality of tangentially oriented slots. When a user inhales through the endpiece, outside air is caused to flow through the tangential slots. This airflow creates a swirling airflow within the chamber 210.

The swirling airflow causes the capsule 225 to contact a partition and then to move within the chamber 210 in a manner that causes the pharmaceutical formulation to exit the capsule 225 and become entrained within the swirling airflow. This version is particularly effective in consistently aerosolizing high doses if the pharmaceutical formulation. In one version, the capsule 225 rotates within the chamber 210 in a manner where the longitudinal axis of the capsule is remains at an angle less than degrees, and preferably less than 45 degrees from the longitudinal axis of the chamber. The movement of the capsule 225 in the chamber 210 may be caused by the width of the chamber 210 being less than the length of the capsule 225. In one specific version, the chamber 210 comprises a tapered section that terminates at an edge. During the flow of swirling air in the chamber 210, the forward end of the capsule 225 contacts and rests on the partition and a sidewall of the capsule 225 contacts the edge and slides and/or rotates along the edge. This motion of the capsule is particularly effective in forcing a large amount of the pharmaceutical formulation through one or more openings 260 in the rear of the capsule 225.

In another version, the dry powder aerosolization apparatus 200 may be configured differently than as shown in FIGS. 8A through 8E. For example, the chamber 210 may be sized and shaped to receive the capsule 225 so that the capsule 225 is orthogonal to the inhalation direction, as described in U.S. Pat. No. 3,991,761 which is incorporated herein by reference. As also described in U.S. Pat. No. 3,991,761, the puncturing mechanism 230 may puncture both ends of the capsule 225. In another version, the chamber may receive the capsule 225 in a manner where air flows through the capsule 225 as described for example in U.S. Pat. No. 4,338,931 and in U.S. Pat. No. 5,619,9S5. In another version, the aerosolization of the pharmaceutical formulation may be accomplished by pressurized gas flowing through the inlets, as described for example in U.S. Pat. No. 5,458,135, U.S. Pat. No. 5,785,049, and U.S. Pat. No. 6,257,233, or propellant, as described in PCT Publication WO 00/72904 and U.S. Pat. No. 4,114,615. All of the above references being incorporated herein by reference in their entireties.

In one version, the powder particles are loaded into a capsule type receptacle and used in an inhaler such as the one shown in FIGS. 8A through 8E. The emitted mass from the capsule is, in one or more embodiments, greater than about 50% w/w, more preferably greater than about 60% w/w, more preferably greater than about 70%, and even more preferably greater than about 80% w/w or greater than about 90% w/w. A relative standard deviation about the emitted dose may be preferably less than 7%, and preferably 4% or less. This provides for excellent dose content uniformity, capable of meeting the increasingly stringent regulatory standards. Composition not formulated in accordance with this invention may not be able to meet this criterion.

Other passive or active dry powder inhalers may alteratively be employed. In one version, a passive dry powder inhaler is preferred because of its ease of use and reproducible aerosolization. Suitable passive dry powder inhalers include both capsule-based inhalers and blister-based inhalers. Capsule-based passive inhalers are particularly preferred due to their larger unit dose volume (compared to current blister devices), which facilitates higher lung doses per puff.

Devices sold or marketed under the following tradenames an/or trademarks may also be suitable: Handihaler (Boehringer Ingelheim), Eclipse (Aventis), AIR inhaler (Alkermes), Cyclohaler (Plastiape), Concept 1 (Novartis), Flowcaps (Hovione), Turbospin (PH&T), Monohaler (Pfizer), Spinhaler (Aventis), Rotahaler (GSK). Suitable blister-based inhalers include: the Diskus and Gemini (GSK), the device of Nektar Therapeutics disclosed in PCT Application No. US2007/022830, which is incorporated herein by reference, Gyrohaler (Vectura), Microdrug, Diskhaler (GSK). Also within the scope of the present invention are active dry powder inhalers including: the Exubera® inhalation device, which is described in U.S. Pat. No. 6,257,233, incorporated herein by reference, Aspirair (Vectura), and Microdose inhaler (Microdose).

Passive devices in combination with the powders of the present invention enable flow-rate independent lung deposition, by balancing the differences in inertial deposition with increases in peak inspiratory flow rate (PIFR) by creating a slightly more dispersed powder. In contrast, active devices may lead to a reverse flow rate dependence, where powder dispersion is constant, but increases in inertial impaction with increases in PIFR may result in lower deposition at the higher PIFR.

The pharmaceutical composition of one or more embodiments of the present invention typically has improved emitted dose efficiency. Accordingly, high doses of the pharmaceutical composition may be delivered using the aerosolization devices and techniques as described herein.

In one or more versions of the present invention, a pharmaceutical composition comprising ciprofloxacin betaine is aerosolizable so that it may be delivered to the lungs of a patient during the patient's inhalation. In this way the ciprofloxacin in the pharmaceutical composition is delivered directly to the site of infection. This is advantageous over systemic administration. Because the active agent(s) often have renal or other toxicity, minimizing systemic exposure often dictates dose. Therefore, the amount of active agent(s) that may be delivered to the lungs via non-pulmonary routes, such as systemic administration, is limited to the minimum pharmacologically effective dose. By administering the active agent(s) by inhalation directly to the lungs, a greater amount may be delivered to the site in need of the therapy while significantly reducing systemic exposure.

One or more embodiments of the pharmaceutical compositions of present invention of are thus effective in the treatment, including adjunctive treatment, of cystic fibrosis.

In one or more embodiments of the invention, a pharmaceutical composition comprising a fluoroquinolone betaine, such as ciprofloxacin betaine, is administered to the lungs of a patient in need thereof. For example, the patient may have been diagnosed with cystic fibrosis, non-CF bronchiectasis, COPD, or hospital-acquired pneumonia.

Thus, the pharmaceutical compositions of one or more embodiments of the present invention can be used to treat and/or provide prophylaxis for a broad range of patients. A suitable patient for receiving treatment and/or prophylaxis as described herein is any mammalian patient in need thereof, in particular a human or animal patient. Examples of patients include, but are not limited to, pediatric patients, adult patients, and geriatric patients.

In one or more versions, an aerosolizeable pharmaceutical composition comprising ciprofloxacin betaine is administered to the lungs of a patient in a manner that results in an effective ciprofloxacin concentration in the lung, in particular the deep lung and/or the upper airways. In one or more embodiments, the amount or concentration of ciprofloxacin and/or ciprofloxacin betaine that reaches the lung is a therapeutic effective amount, such as an amount effective to treat CF. In one or more embodiments an amount per dose of ciprofloxacin betaine that reaches the lungs may be from about 10 mg to about 50 mg, such as about 30 mg to about 40 mg.

In one or more embodiments, a therapeutic dose of ciprofloxacin betaine is delivered to a patient in need thereof in three or four inhalations or less, such as in two inhalations, or in a single inhalation. In preferred embodiments, a therapeutic dose of ciprofloxacin betaine is delivered to a patient in need thereof in three inhalations or less, such as in two inhalations, or in a single inhalation. In one or more embodiments, a therapeutic dose of ciprofloxacin betaine is delivered in less than about three minutes, preferably less than about two minutes, or less than about one minute.

In one or more embodiments, administration of a an inhalable formulation of ciprofloxacin betaine to a cystic fibrosis patient in accordance with the compositions and devices described herein results in significant improvements in quality of life, or improvements in treatment compliance, or both.

The ciprofloxacin betaine treatment regimen of the present invention may be used alone or in combination with an agent for the treatment of endobronchial infections, particularly infections by *P. aeruginosa*. In this aspect of the invention, the one or more agent for the treatment of endobronchial infections may be an antibiotic, and may be administered during the first treatment period of ciprofloxacin betaine (or other fluoroquinolone betaine) treatment, during the second non-treatment period wherein no ciprofloxacin betaine is administered to the endobronchial system of the patient, or during both the first and second treatment periods. In one embodiment of this aspect of the invention, the one or more agent for the treatment of endobronchial infections is administered during the second non-treatment period wherein no ciprofloxacin betaine is administered to the endobronchial system of the patient. Suitable agents for the treatment of endobronchial infections include, for example, aminoglycosides such a tobramycin, non-aminoglycoside antiinfective agents, such as monobactam, β-lactam, macrolide, and/or glycopeptide antibiotic compounds. For example, the non-aminoglycoside antiinfective agent may be aztreonam.

In one particular treatment regimen of the present invention, the fluoroquinolone betaine, such as ciprofloxacin betaine, is administered during off-periods of tobramycin treatment. For example, tobramycin may be administered for an on-period (such as about a month) and then not administered during an off-period (such as about a month). In this version, the powder according to the present invention is administered during the off-period. The present powder may alternatively or additionally be administered during the on-period. The on-period and off-periods may be a day, several days, a week, several weeks, 28 days, a month, or several months or mixtures thereof.

In other versions, the composition may comprise one or more active agents other than the fluoriquinolones described above. For example, any insoluble and/or crystalline active agent may be formulated in accordance with the present invention.

The foregoing description will be more fully understood with reference to the following Examples. Such Examples, are, however, merely representative of methods of practicing one or more embodiments of the present invention and should not be read as limiting the scope of the invention.

EXAMPLES

Example 1

Water Solubility of Ciprofloxacin as a Function of pH

Figure 2:
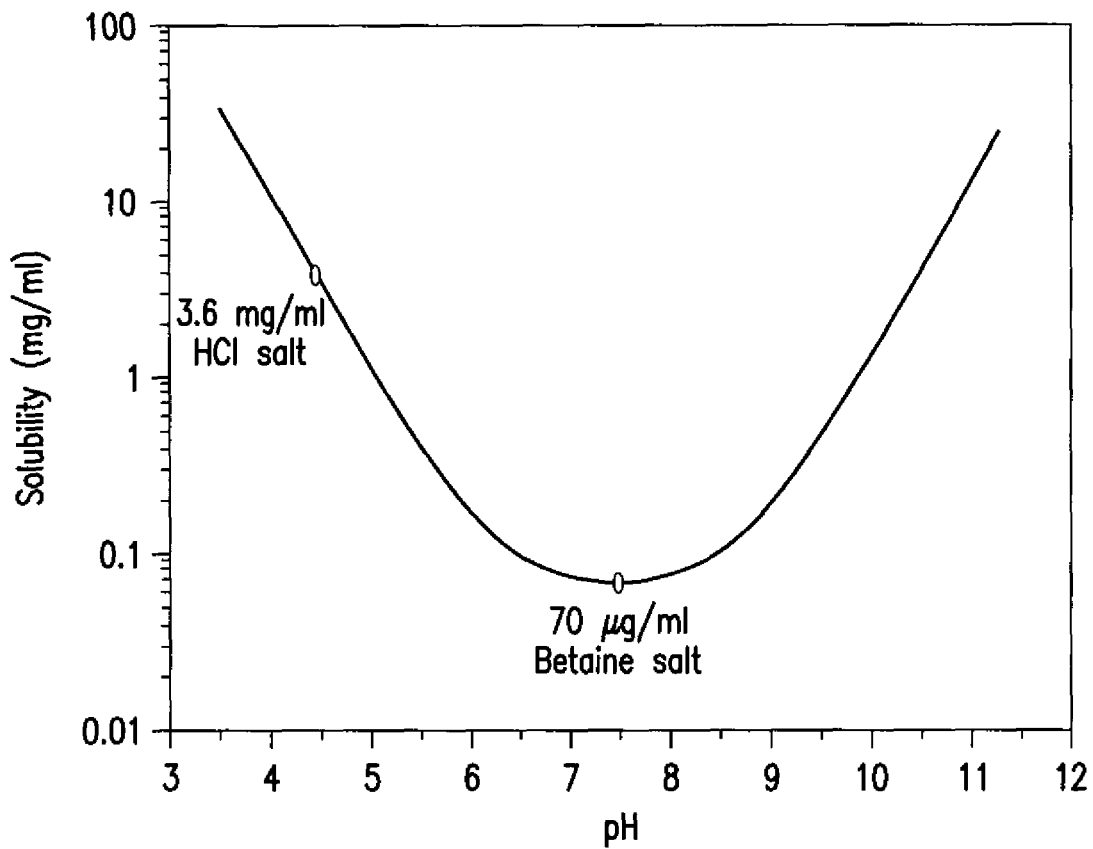

The water solubility of ciprofloxacin is dependent on the solution pH (FIG. 2). Below the pK of the carboxylic acid ($pK_1$=6.0), the drug exists as the hydrochloride salt, and is highly water soluble. The drug is also soluble above the pK of the amine group ($pK_2$=8.8). The solubility of the zwitterionic ciprofloxacin betaine near neutral pH drops precipitously to about 70 µg/ml.

Example 2

Dynamic Vapor Sorption of Ciprofloxacin Powders

In one version, a powder formulation comprises about 65% w/w ciprofloxacin betaine 3.5 hydrate, about 20% w/w distearoylphosphatidylcholine, and about 2% w/w calcium chloride dehydrate with about 12% w/w water, and less than 1% w/w residual perfluorooctyl bromide. This formulation will hereinafter be referred to as CIP (ciprofloxacin inhalation powder).

The equilibrium moisture sorption isotherms (25° C.) of CIP, drug substance, and placebo powder are shown in FIG. 3. All isotherms were measured using gravimetric water vapor sorption. To assess the accuracy of the isotherm of CIP, a sample of powder was equilibrated at 25° C./60% RH and its water content was measured using Karl Fischer titrimetry. The good agreement between the measured water content and the value given by gravimetric vapor sorption indicates that the latter technique provides an accurate measure of the isotherm. The kinks in the isotherm of Ciprofloxacin drug substance are characteristic of a crystalline material that forms stoichiometric hydrates. The discontinuities in the slope of the isotherm at approximately 5%, 17%, and 65% RH are due to hydrate-to-hydrate transformations. Across the range of RH values studied, the most stable solid-state composition lies in the broad, shallow region between 20% and 60% RH. The composition in this region is consistent with that of Ciprofloxacin.3.5 $H_2O$ (or Ciprofloxacin$_2$.7 $H_2O$), which has a theoretical water content of 16.0% $H_2O$ (w/w). The identification of the crystalline 3.5 hydrate was confirmed by Raman spectroscopy (data not shown). The moisture sorption isotherm of CIP is qualitatively and quantitatively related to the isotherms of its components, Ciprofloxacin drug product and the spray-dried placebo (a pseudocomponent comprising DSPC and $CaCl_2$). Qualitatively, the isotherm of CIP has features of the isotherms of its components; the CIP isotherm exhibits the steps characteristic of Ciprofloxacin drug substance and a slightly greater slope at each point (as compared to the isotherm of the drug substance) due to the presence of DSPC/$CaCl_2$. Quantitatively, the isotherm of CIP is approximately a linear superposition of the isotherms of Ciprofloxacin drug substance and placebo. That is, the CIP isotherm is about 69% of the distance between the isotherms of its main components, as would be expected from the drug content of CIP (nominally 70%). This is not unexpected. Because the drug and the phospholipid in CIP are predominantly in separate phases, the isotherm of the formulated material will be approximately equal to a weighted sum of the isotherms of its constituents.

In the range from roughly 20% RH to 65% RH, ciprofloxacin betaine is present as the 3.5 hydrate. This corresponds to a moisture content in the spray-dried powder between about 10% and 15% w/w. The identification of the 3.5 hydrate for the spray-dried powders was confirmed by Raman spectroscopy. The 3.5 hydrate has been observed to be stable on storage.

Example 3

Preparation of Ciprofloxacin Inhalation Powder

Ciprofloxacin Inhalation Powder (CIP) was developed with the specific goal of improving the targeting of ciprofloxacin to the bronchial airways as compared to oral and parenteral administration, while also improving patient convenience (i.e., increased portability, and reduced administration times) relative to current nebulized antibiotics.

CIP was produced by spray drying a homogenized submicron oil-in-water emulsion of perflubron (perfluorooctyl bromide, PFOB) and water for irrigation (WFIr), containing 1,2-distearoyl-sn-glycero-3-phosphocholine (DSPC), calcium chloride and suspended ciprofloxacin betaine in amounts as shown in Table 2 below. The micronized ciprofloxacin betaine particles were prepared by standard jet milling processes, or by high pressure homogenization. The composition of the suspension-based feedstock for a target 1 kg batch size is detailed in Table 2. The volume fraction of the dispersed PFOB is about 0.1, and the ratio of PFOB/DSPC about 20/1 w/w.

TABLE 2

Composition of the feedstock used to prepare 1 kg of CIP

| Component | Target Quantity Per 1000 g Total Batch Size |
|---|---|
| Ciprofloxacin betaine | 700.0 |
| 1,2-distearoyl-sn-glycero-3-phosphocholine (DSPC) | 280.0 |
| Calcium Chloride Dihydrate | 20.0 |
| Perflubron [Perfluorooctyl bromide (PFOB)][1] | 5760.0 |
| Water for Irrigation (WFIr)[2] | 30333.0 |

[1]Used as processing agent, removed to residual levels during processing
[2]Used as a processing agent, mainly removed during processing The feedstock was prepared by first dispersing the DSPC and CaCl$_2$ in warm WFIr with the aid of a high speed mixer (e.g., UltraTurrax) to form multilamellar liposomes. PFOB is then added slowly while mixing to form a coarse emulsion. The droplet size of the resulting emulsion is then reduced by high pressure homogenization with a piston gap homogenizer or Microfluidizer. The micronized drug is then added to the emulsion to create the desired suspension-based feedstock. The PFOB and water phases of the drug-containing emulsion/suspension feedstock are evaporated via spray-drying on a Niro Mobile Minor spray-drier, leaving the ciprofloxacin betaine, DSPC and calcium chloride in dry particle form. The spray-dried particles contain residual water and PFOB as shown in Table 4.

TABLE 3

Composition of spray-dried CIP

| Component and Quality Standard | | Function | Strength (label claim) 50 mg/capsule Nominal Quantity per capsule (mg) | % w/w |
|---|---|---|---|---|
| Ciprofloxacin | USP | Active Pharmaceutical Ingredient | 32.5 | 65 |
| 1,2-distearoyl-sn-glycero-3-phosphocholine (DSPC) | Non-Compendial (In House) | Emulsion stabilizer, dispersion enhancer, and particle-forming agent | 10 | 20 |
| Calcium Chloride, dihydrate | USP/EP/JP | Particle-stabilizing agent | 1 | 2 |
| Water for Irrigation (WFIr)[1] | USP | Processing aid | 6 | 12 |
| Perflubron [Perfluorooctyl bromide (PFOB)][2] | USP | Processing aid | 0.5 | 1 |
| Total | | | 50 | 100 |

[1]Used as processing aid; mainly removed during processing

[2]Used as processing aid; removed to residual levels during processing

All compendial excipients used are in compliance with the requirements in the respective monographs in USP/NF.

The formulated bulk powder is filled into individual, inhalation-grade, clear, size 2 hydroxypropylmethylcellulose (HPMC) capsules nominally containing 50 mg of CIP (CIP contains approximately 65% ciprofloxacin betaine, therefore each capsule contains 32.5 mg, or at least about 32 mg, of ciprofloxacin betaine).

Example 4

Physicochemical Properties of CIP Bulk Powder

The physicochemical properties of the four lots of CIP bulk powder from Example 3 are presented in Table 4. Ciprofloxacin identity, content and purity were determined by reverse phase high performance liquid chromatography (RP-HPLC) with UV detection (according to Ph. Eur. Monograph for Ciprofloxacin). Identity testing of CIP consisted of a retention time criterion (sample ciprofloxacin peak retention time must be within 0.5 minutes of that of the reference standard), and a UV spectrum criterion (sample ciprofloxacin UV spectrum has a peak absorbance at 278±2 nm). Ciprofloxacin content was determined against a reference standard, and purity was calculated by area normalization. The Ciprofloxacin content has an acceptance criterion of 90 to 110% of the target mean content (target=32.5 mg) of Ciprofloxacin per capsule. The Ciprofloxacin impurities B, C, and D defined in EP are quantitated, and an acceptance criterion for each impurity of ≤0.50% was applied.

Water content of CIP was measured using coulometric Karl Fischer titrimetry. The Karl Fischer system consists of a Metrohm model 831 Karl Fischer Coulometer, a model 800 Dosino, and a model 774 Oven Sample Processor. To analyze a sample, the autosampler inserts the sample vial into the oven at 140° C. Dry nitrogen (60±5 mL/min) flows over the heated sample to carry the evaporated water to the titration cell where it reacts with the dry Karl Fischer reagent. The titration ends when the relative stop drift reaches 5 μg/min. The system performance was checked by measuring the water content of standard samples of potassium citrate monohydrate (Hydranal®-Water Standard KF Oven, Riedel de Haën, 34748) before and after measurements of the samples of unknown water content. For each sample, between 10 and 70 mg of CIP powder was weighed into a glass vial, which was crimped and placed on the autosampler. Samples were prepared in triplicate. To assess the water contributed from the KF system and the environment, three empty "blank" vials were prepared at the same (RH and temperature) conditions as used for preparation of the powder samples. The average blank water content was subtracted from the water titrated from each sample.

The residual perflubron in bulk powder was measured by gas chromatography with flame ionization detection. The percent of residual perflubron in CIP bulk powder was determined against a USP reference standard for perflubron. The limit of quantitation was 0.05% w/w.

A Microbial Limit Test (MLT) was performed to confirm that the microbial content of the powder with the capsules conforms to FDA draft guidance requirements and European Pharmacoepia. The acceptance limits of total aerobic microbial count and total yeasts and molds were chosen based on the limits for inhalation products proposed in the Pharmacopeial Forum Vol. 29(5), p. 1733. The acceptance limits of Gram-negative bacteria and enterobacteriaceae were chosen to comply with the requirements according to Ph. Eur. 5.1.4 for products for use in the respiratory tract. The acceptable limit for specific pathogens was chosen based on USP <61>.

TABLE 4

Physicochemical properties of CIP bulk powder

| Attributes | Acceptance Criteria and Reported Information | Lot 10744 | Lot 10857 | Lot 10858 |
|---|---|---|---|---|
| Ciprofloxacin Content | 0.553 mg/mg to 0.748 mg/mg | 0.659 | 0.652 | 0.657 |
| Ciprofloxacin Purity | Report | 99.95% | 99.95% | 99.93 to 99.98% |
| Individual Impurities ≥0.10% | Report | None | None | None |
| Water Content | Report | 12.2% | 11.9% | 12.1% |
| pH | Report | 7.4 | 6.7 | 6.8 |
| Residual Perflubron | NMT 1.00% w/w | <0.05% to 0.05% | <0.05% | <0.05% |
| Primary Particle Size | X50: NMT 5.0 μm | 2.5 μm | 2.5 μm | 2.5 μm |
| Microbial Limits | Total Aerobic Microbial Count NMT 100 CFU/g | <50 CFU/g | <50 CFU/g | <50 CFU/g |
| | Total Combined Yeasts and Molds NMT 10 CFU/g | <10 CFU/g | <10 CFU/g | <10 CFU/g |
| | Other Gram Negative Bacteria NMT 10 CFU/g | <1 CFU/g | <1 CFU/g | <1 CFU/g |
| | Absent for: *Pseudomonas aeruginosa, Staphylococcus aureus, Escherichia coli, Salmonella* species, *Enterobacteriaceae* | Pass | Pass | Pass |

CFU = Colony Forming Units;
NLT = Not less than;
NMT = Not more than;
RSD = Relative Standard Deviation The Ciprofloxacin content is well controlled within the acceptance criteria. The spray-drying process has a negligible impact on the purity of the drug substance, as the purity was maintained at >99.93% for all four lots, with no single impurity greater than 0.1%. The impurity profile of ciprofloxacin is well characterized and controlled by the drug substance specifications in accordance with USP and EP monographs. Impurities B, C, and D are the only detectable impurities in the drug substance, and impurity C is the only related substance that is also a degradant of ciprofloxacin. The other known ciprofloxacin impurities (E and F), though listed in the EP <1089>, are not present in either the ciprofloxacin raw material or the formulated product. None of the individual impurities was present at levels greater than 0.1% w/w in CIP.

Because the engineered particles are prepared from an aqueous suspension of drug, the primary particle size is controlled to a large extent by the particle size distribution of the drug substance. For the four lots detailed in Table 4, the $x_{50}$ was between 2.4 μm and 2.5 μm (2 bar dispersing pressure).

The residual levels of perflubron are at or below the limit of quantitation for three lots tested (LOQ=0.05%), and just above the LOQ (0.07%) for the fourth lot. The low residual levels indicate that the process aid is efficiently removed in the manufacturing process (see Table 4).

Microbial limit testing, total yeasts and molds, and specific pathogens were all within the acceptance criteria established for dry powder inhalation products.

Example 5

Aerosol Properties of CIP-001

The aerosol properties of three lots of CIP made according to Example 3 were delivered from a portable passive dry powder inhaler (i.e. an inhaler as shown in FIGS. 8A through 8E) are illustrated in Table 5.

The mean emitted powder mass was typically greater than 90% w/w with RSD values typically less than 5%. The mass median aerodynamic diameter was about 3.6 μm, with a FPF<4.7 μm of about 60% w/w of the nominal dose. The resulting FPD<4.7 μm following inhalation of a 32.5 mg ciprofloxacin betaine dose was expected to provide a therapeutic dose in less than 3 puffs or less than 2 puffs, such as a single puff.

TABLE 5

Aerosol properties of CIP delivered from FIG. 8 inhaler

| Attribute | Acceptance Criteria | Lot 10744 | Lot 10857 | Lot 10858 |
|---|---|---|---|---|
| Emitted Powder Mass | Mean Emitted Powder Mass | 45.7 mg | 47.9 mg | 47.5 mg |
| | % RSD | 9.1% | 1.8% | 1.5% |
| | # of actuations outside 75-125% of mean | 0 | 0 | 0 |
| | # of actuations outside 65-135% of mean | 0 | 0 | 0 |

TABLE 5-continued

Aerosol properties of CIP delivered from FIG. 8 inhaler

| Attribute | Acceptance Criteria | Lot 10744 | Lot 10857 | Lot 10858 |
|---|---|---|---|---|
| Aerodynamic Particle Size Distribution | MMAD | 3.6 µm | 3.6 µm | 3.7 µm |
| | FPD < 4.7 µm | 20.2 mg | 19.5 mg | 18.9 mg |
| | FPF % < 4.7 µm | 62% | 60% | 58% |
| | mean mg of Ciprofloxacin mass per stage and filter | Stage 0: 0.3 mg | Stage 0: 0.3 mg | Stage 0: 0.3 mg |
| | | Stage 1: 1.0 mg | Stage 1: 1.1 mg | Stage 1: 1.2 mg |
| | | Stage 2: 3.3 mg | Stage 2: 3.4 mg | Stage 2: 3.6 mg |
| | | Stage 3: 10.4 mg | Stage 3: 10.3 mg | Stage 3: 10.1 mg |
| | | Stage 4: 7.1 mg | Stage 4: 6.8 mg | Stage 4: 6.5 mg |
| | | Stage 5: 2.0 mg | Stage 5: 1.9 mg | Stage 5: 1.8 mg |
| | | Stage 6: 0.1 mg | Stage 6: 0.2 mg | Stage 6: 0.2 mg |
| | | Stage 7: 0.0 mg | Stage 7: 0.0 mg | Stage 7: 0.0 mg |
| | | Filter: 0.5 mg | Filter: 0.4 mg | Filter: 0.4 mg |

Example 6

Storage Stability of CIP Formulations

The storage stability of CIP formulation from Example 3 at 25° C./60% RH (Table 6), and 40° C./75% RH (Table 7) is detailed below. CIP exhibits excellent physical, chemical, and aerosol stability over thirty months at 25° C./60% RH, and 6 months at 40° C./75% RH.

TABLE 6

Stability summary for CIP Lot 10655 (T = 25 ± 2° C./ 60% RH ± 5% RH)

| Attribute | Initial | 1 mo | 3 mo | 6 mo | 12 mo | 18 mo | 24 mo | 30 mo |
|---|---|---|---|---|---|---|---|---|
| Ciprofloxacin Content | 33.5 mg | 33.6 mg | 32.2 mg | 33.3 mg | 33.5 mg | 33.1 mg | 33.1 mg | 34.0 mg |
| Ciprofloxacin Purity | 99.95% | 99.95% | 99.96% | 99.94% | 99.95% | 99.96% | 99.95% | 99.95% |
| Individual Impurities ≥0.10% | None | None | None | None | None | None | None | None |
| Water Content | 12.3% | 12.5% | 12.4% | 12.5% | 12.8% | 13.8% | 12.9% | 13.0% |
| Mean Emitted Powder Mass (RSD) | 93.0% | 92.6% | 90.8% | 91.6% | 93.4%. | 93.4% | 93.0% | 93.0% |
| Emitted Powder Mass % RSD | 2.8 | 3.1 | 7.6 | 1.7 | 2.4 | 3.1 | 2.1 | 1.9 |
| Mass Median Aerodynamic Diameter | 3.6 µm | 3.6 µm | 3.6 µm | 3.5 µm | 3.6 µm | 3.6 µm | 3.6 µm | 3.6 µm |
| Fine Particle Dose <4.7 µm | 19.0 mg | 18.2 mg | 18.5 mg | 18.2 mg | 17.8 mg | 16.9 mg | 18.1 mg | 17.9 mg |

TABLE 7

Stability summary for CIP Lot 10655 (T = 40 ± 2° C./75% RH ± 5% RH)

| Attributes | Initial | 1 month | 3 month | 6 month |
|---|---|---|---|---|
| Ciprofloxacin Content | 33.5 mg | 33.6 mg | 33.3 mg | 33.7 mg |
| Ciprofloxacin Purity | 99.95% | 99.96% | 99.96% | 99.94% |
| Individual Impurities ≥0.10% | None | None | None | None |
| Water Content | 12.3% | 12.6% | 12.4% | 12.8% |
| Mean Emitted Powder Mass (RSD) | 93.0% | 94.4% | 93.8% | 95.2% |
| Emitted Powder Mass % RSD | 2.8 | 4.0 | 1.9 | 2.4 |
| Mass Median Aerodynamic Diameter | 3.6 µm | 3.6 µm | 3.6 µm | 3.6 µm |
| Fine Particle Dose <4.7 µm | 19.0 mg | 18.3 mg | 19.1 mg | 18.6 mg |

No significant changes in ciprofloxacin content, ciprofloxacin purity, water content, mean emitted powder mass and % RSD, mass median aerodynamic diameter and fine particle dose <4.7 µm were observed under either storage condition.

Example 7

Impact of Formulation Composition of Powder Properties

Figure 4A:
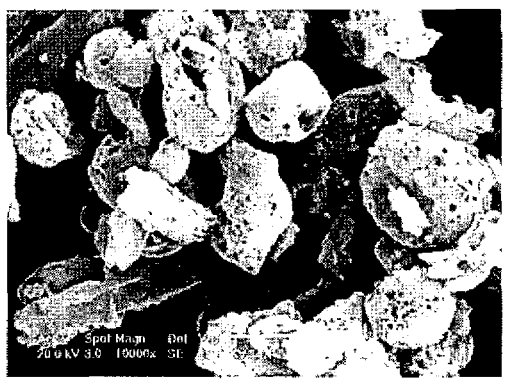
FIG. 4A-4D are scanning electron micrographs of micronized ciprofloxacin betaine (FIG. 4B, 4D) and ciprofloxacin betaine inhalation powder according to the present invention, CIP, bulk powder (FIG. 4A, 4C) at magnifications of 10,000× and 20,000×, respectively.
Figure 4B:
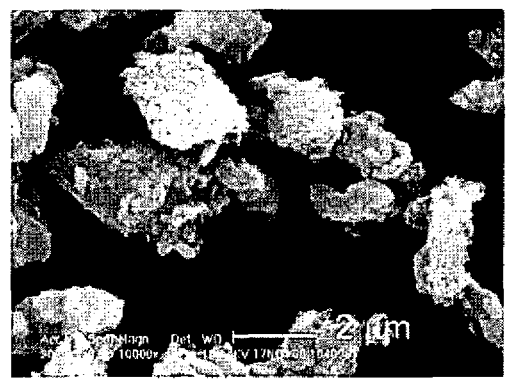
Figure 4C:
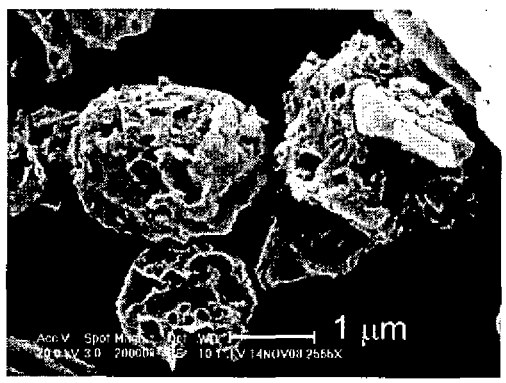
Figure 4D:
Figure 5A:
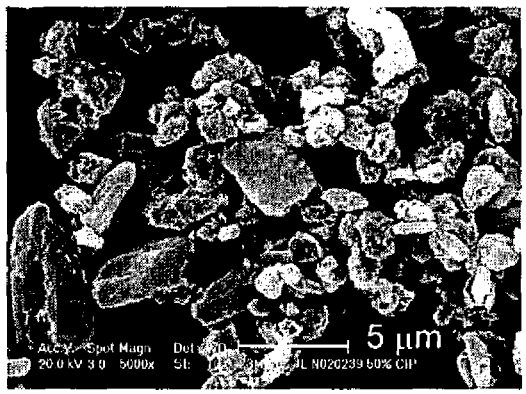
FIG. 5A-5F are scanning electron micrographs of several spray-dried ciprofloxacin betaine inhalation powder, CIP, formulations containing differing drug contents. 5(A): 50%, lot N020239; 5(B): 50%, lot N020242; 5(C): 60%, lot N020240; 5(D): 60%, lot N020243; 5(E): 70%, lot N020241; and 5(F): 70%, lot N020244.
Figure 5B:
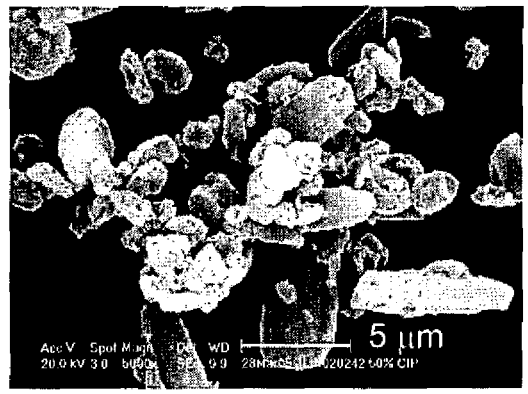
Figure 5C:
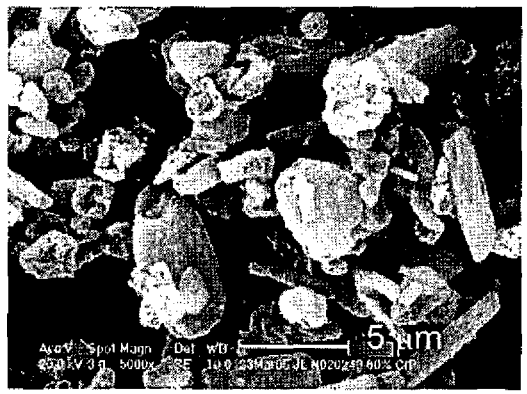
Figure 5D:
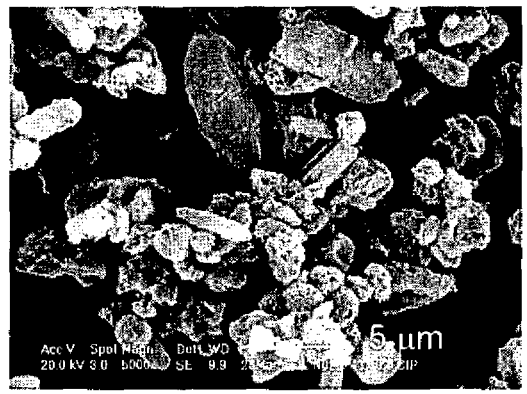
Figure 5E:
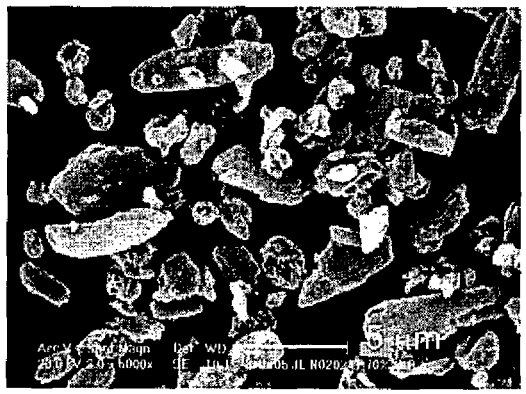
Figure 5F:
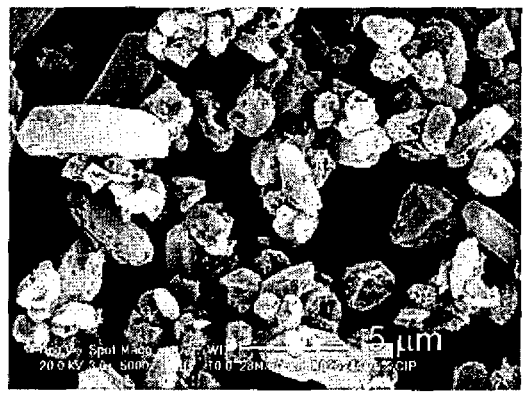

The impact of formulation variations on CIP powder properties is illustrated in Table 8. The powders were prepared as described in Example 3. These lots were manufactured with a Buchi spray-dryer. Scanning electron microscopy (SEM) was used to qualitatively assess the morphology of the spray-dried particles (FIG. 5A-5F). To this end, samples were mounted on silicon wafers that were then mounted on top of double-sided carbon tape on an aluminum SEM stub. The mounted powders were sputter-coated with gold-palladium in a Denton sputter-coater for 60-90 seconds at 75 mTorr and 42 mA. This produces a coating thickness of approximately 150 Å. Images were taken with a Philips XL30 ESEM using a $LaB_6$ source operated in high vacuum mode using an Everhart-Thomley detector to capture secondary electrons for the image composition. The accelerating voltage was set at 20 kV and the beam current was set at 33 mA. The working distance was between 5 and 6 mm. Micronized ciprofloxacin betaine is characterized by flat, plate-like crystals, with a broad distribution of sizes ranging from tens of nanometers to several microns (FIG. 4B, 4D). The nanocrystalline drug is present as agglomerates with the larger crystals. The large area of contact for the flat crystals leads to strong interparticle cohesive forces. In contrast, spray-dried CIP bulk powder has a more spheroidal appearance with fewer nano-sized particles. The porous surface morphology characteristic of particles manufactured using the PulmoSphere process is clearly evident (FIG. 4A, 4C, 5A-5F). No changes in the bulk powder properties (MMS, Purity, Moisture Content) with variations in drug loading in the range from 50% to 70% w/w.

TABLE 8

Impact of drug loading on powder properties of ciprofloxacin betaine spray-dried particles

| Lot # | % Drug (w/w) | % DSPC (w/w) | % CaCl$_2$ (w/w) | MMD (μm) | Purity (%) | Moisture Content (%) |
|---|---|---|---|---|---|---|
| N020239 | 50 | 46.7 | 3.3 | 2.1 | 99.9 | 10.5 |
| N020240 | 60 | 37.4 | 2.6 | 2.2 | 99.9 | 11.5 |
| N020241 | 70 | 28.0 | 2.0 | 2.2 | 99.9 | 12.3 |
| N020242 | 50 | 46.7 | 3.3 | 2.3 | 99.9 | 10.8 |
| N020243 | 60 | 37.4 | 2.6 | 2.2 | 99.9 | 11.7 |
| N020244 | 70 | 28.0 | 2.0 | 2.2 | 99.9 | 12.4 |

The aerosol properties of the above formulations are detailed in Table 9. Variations in drug loading (including drug content up to 70%) did not alter the desired aerosol properties, of ED, MMAD and FPF. Hence, drug loadings of 50 or 60 or 70% w/w are within the preferred scope of the present invention.

TABLE 9

Aerosol properties of spray-dried ciprofloxacin betaine particles as a function of drug content.

| Lot# | Emitted Dose (%) | MMAD (μm) | % FPF < 4.7 μm |
|---|---|---|---|
| N020239 | 93 ± 0.6 | 3.7 | 55 |
| N020240 | 93 ± 1.1 | 3.6 | 55 |
| N020241 | 94 ± 1.9 | 3.6 | 54 |
| N020242 | 95 ± 0.9 | 3.6 | 60 |
| N020243 | 95 ± 1.1 | 3.7 | 51 |
| N020244 | 94 ± 4.2 | 3.7 | 49 |

Example 8

Physicochemical Properties of Micronized Ciprofloxacin Betaine and CIP

The surface properties of CIP powders prepared by spray-drying a complex feedstock comprising micronized ciprofloxacin betaine dispersed in the continuous phase of an oil-in-water emulsion are presented in Table 10. Significant increases in specific surface area, porosity, and rugosity Sv are observed for the phospholipid-coated particles relative to micronized drug. Increases in surface roughness and/or porosity are expected to reduce interparticle cohesive forces for engineered particles, thereby improving powder fluidization and dispersibility. This ultimately drives the excellent aerosol performance observed (high emitted mass, low RSD), and the improved aerosol targeting to the lungs.

TABLE 10

Surface properties of micronized ciprofloxacin and spray-dried CIP

| Lot # | Identity | Specific Surface Area (m$^2$/g) | Porosity (cm$^3$/g) | Sympatec Sv (m$^2$/cm$^3$) | Rugosity Sv* |
|---|---|---|---|---|---|
| BXA1GE7 | API | 4.4 | 2.7 | 4.91 | 1.1 |
| 2501X | CIP | 11.0 | 10.0 | 3.16 | 5.0 |
| 2565X | CIP | 10.9 | 9.2 | 3.50 | 4.5 |

*API shape factor = 1.27

Example 9

Impact of Surface Roughness on Powder Dispersion

The relative dispersibility of powder formulations can be studied with the laser diffraction technique by varying the dispersing pressure in the RODOS disperser. A comparison of micronized ciprofloxacin betaine and CIP bulk powder is presented in FIG. 6. While both curves converge to an $x_{50}$ of 2.3 to 2.4 μm at a dispersing pressure of ca. 4 bar, the curves diverge significantly at lower dispersing pressures. The $x_{50}$ of micronized ciprofloxacin betaine at a dispersing pressure of 0.2 bar is 3.5 μm, while the $x_{50}$ for the spray-dried CIP powder was 2.9 μm. The ratio of the median particle sizes measured at low and high dispersing pressures is a measure of the dispersibility of the powder. In the present study, the dispersibility index, δ, is equal to 0.67 for micronized drug versus 0.78 for the spray-dried powder. Hence, the spray-dried CIP powder disperses at much lower energies than does the micronized drug.

Example 10

Effect of PFOB Volume Fraction on CIP Powder Properties

The effect of PFOB volume fraction on CIP powder properties is illustrated in Table 12 and Table 13. The powders were prepared as described in Example 3 at a 100 g batch size and the spray-drying feedstock compositions are described in Table 11. These lots were manufactured on a Niro Mobile Minor spray-dryer as described in Example 3 and tested in the same manner as Examples 4 and 5.

TABLE 11

The spray-dried feedstock composition of the feedstock used to prepare 100 g lots of CIP

| | Target Quantity Per 100 g nominal Batch Size | | | |
|---|---|---|---|---|
| Component | 9.0% w/v PFOB | 6.75% w/v PFOB | 4.5% w/v PFOB | 0% w/v PFOB |
| Ciprofloxacin betaine | 70.0 | 70.0 | 70.0 | 70.0 |
| 1,2-distearoyl-sn-glycero-3-phosphocholine (DSPC) | 28.0 | 28.0 | 28.0 | 28.0 |
| Calcium Chloride Dihydrate | 2.0 | 2.0 | 2.0 | 2.0 |
| Perflubron [Perfluorooctyl bromide (PFOB)] | 576.0 | 432.0 | 288.0 | 0.0 |
| Water for Irrigation (WFIr) | 3033.0 | 3108.0 | 3183.0 | 3333.0 |

Variation in PFOB volume fraction from 4.5% to 9% w/v in the ciprofloxacin betaine spray-drying feedstock did not alter the primary particle size ($x_{10}$, $x_{50}$, and $x_{90}$) (Table 12) and ciprofloxacin content or the desired aerosol properties, of EM, MMAD and FPF (Table 13). However, if no PFOB is present, the primary particle size characteristics shifts toward smaller particles, as it does not create the porous DSPC coating on the ciprofloxacin betaine spray-dried particles (Table 12). Moreover, the absence of PFOB in the spray-drying feedstock led to particles which fluidize and disperse less efficiently from the filled capsules (Table 13). The decreases in powder fluidization are reflected in the decreased mean emitted mass (82% vs. 93-94%), and the higher variability in the emitted mass (RSD=9.4% vs. ≤1.0%) versus those formulations comprising a pore-forming agent. The decreases in powder dispersibility for the formulation sans pore-forming agent are reflected in the increased MMAD and decreased FPF. Although these differences appear relatively small under the test conditions employed (Q=60 LPM, V=2 L), it is expected that the magnitude of the differences between the formulations will be further exacerbated at the low flow rates and inhaled volumes anticipated for some CF patients. Hence, CIP spray-drying feedstocks with PFOB volume fractions greater than 4.5% w/v are preferred within the scope of the present invention.

TABLE 12

Effect of PFOB volume fraction on CIP bulk powder properties

| Lot # | PFOB (% w/v) | Primary Particle Size via Sympatec (µm) | Ciprofloxacin Content (%) |
|---|---|---|---|
| N020486-1 | 9 | $x_{10}$: 1.02<br>$x_{50}$: 2.56<br>$x_{90}$: 5.03 | 0.654 |
| 2438X | 6.75 | $x_{10}$: 0.98<br>$x_{50}$: 2.59<br>$x_{90}$: 5.41 | 0.668 |
| N020486-2 | 4.5 | $x_{10}$: 1.02<br>$x_{50}$: 2.52<br>$x_{90}$: 5.13 | 0.649 |
| N020486-3 | 0 | $x_{10}$: 0.68<br>$x_{50}$: 2.36<br>$x_{90}$: 5.35 | 0.639 |

TABLE 13

Effect of PFOB volume fraction on CIP bulk aerosol properties

| Lot # | PFOB (% w/v) | Emitted Mass ± RSD (%) | MMAD (µm) | FPF < 4.7 µm (%)[1] |
|---|---|---|---|---|
| N020486-1 | 9 | 94 ± 0.7 | 3.7 | 76 |
| 2438X | 6.75 | 94 ± 0.9 | 3.7 | 75 |
| N020486-2 | 4.5 | 93 ± 1.0 | 3.7 | 75 |
| N020486-3 | 0 | 82 ± 9.4 | 3.9 | 68 |

[1] Expressed as the FPF on the impactor stages, not as a percentage of the nominal dose.

Example 11

Impact of Ciprofloxacin Betaine Crystal Size on Aerosol Properties of Spray-Dried CIP The impact of the particle size distribution of micronized ciprofloxacin betaine on the aerosol properties of the resulting spray-dried CIP powders is presented in Table 14.

TABLE 14

Impact of ciprofloxacin betaine crystal size on aerosol properties of CIP

| | API | | | CIP | | |
|---|---|---|---|---|---|---|
| | | | | | FPF < | |
| Lot # | $x_{50}$ (µm) | $x_{90}$ (µm) | EM ± SD (%) | MMAD (µm) | 4.7 µm (%) | FPD < 4.7 µm (mg) |
| BV01VLH | 2.24 | 4.43 | 93 ± 1.8 | 2.8 | 71 | 24.7 |
| BX01V3U | 2.98 | 6.89 | 94 ± 1.5 | 3.4 | 60 | 19.5 |
| BX01VLJ | 4.34 | 10.34 | 92 ± 1.8 | 4.1 | 46 | 16.0 |

Significant increases in MMAD and decreases in FPF and FPD are noted with increases in the size of the ciprofloxacin drug crystals. Of note is the observation that powder fluidization, which is driven by the porous nature of the phospholipid coating on the drug crystals is maintained irregardless of crystal size.

Example 12

Pharmacokinetics of Inhaled CIP

The pharmacokinetics of ciprofloxacin was studied in healthy volunteers and in CF patients following inhalation of a single dose of CIP. Plasma and sputum pharmacokinetics are shown in Table 15 and Table 16, respectively. Compared to inhaled ciprofloxacin HCl which has a lung half-life in rats of less than 1 h, CIP has an extended lung residence time (sputum half-life=5.5 h to 9.0 h, depending on dose). Very low systemic levels of ciprofloxacin are observed.

The improved lung targeting for inhaled CIP relative to orally administered ciprofloxacin is presented in FIG. 7. Lung targeting, expressed as the ratio of the Sputum AUC/Plasma AUC is more than 250-fold higher for inhaled CIP.

TABLE 15

Plasma pharmacokinetics for inhaled CIP

| | Study 1: Healthy Subjects | | Study 2: Patients with CF | | | |
|---|---|---|---|---|---|---|
| | 50 mg CIP (32.5 mg ciprofloxacin) N = 6 | | 50 mg CIP (32.5 mg ciprofloxacin) N = 6 | | 100 mg CIP (65 mg ciprofloxacin) N = 6 | |
| Dose Parameter | Geometric Mean | Geometric CV (%) | Geometric Mean | Geometric CV (%) | Geometric Mean | Geometric CV (%) |
| AUC (mg*h/L) | 0.354 | 30.3 | 0.425 | 12.1 | 1.00 | 15.1 |
| $C_{max}$ (mg/L) | 0.056 | 32.2 | 0.079 | 19.2 | 1.82 | 17.4 |

TABLE 15-continued

Plasma pharmacokinetics for inhaled CIP

| | Study 1: Healthy Subjects | | Study 2: Patients with CF | | | |
|---|---|---|---|---|---|---|
| | 50 mg CIP (32.5 mg ciprofloxacin) N = 6 | | 50 mg CIP (32.5 mg ciprofloxacin) N = 6 | | 100 mg CIP (65 mg ciprofloxacin) N = 6 | |
| Dose Parameter | Geometric Mean | Geometric CV (%) | Geometric Mean | Geometric CV (%) | Geometric Mean | Geometric CV (%) |
| $t_{max}$ (h) | 0.63 | 0.25-1.50 | 1.5 | 0.5-2.0 | 1.26 | 0.75-1.50 |
| $t_{1/2}$ (h) | 9.54 | 19.66 | 6.30 | 66.8 | 8.06 | 37.0 |
| MRT (h) | 10.68 | 14.81 | 6.48 | 37.7 | 7.27 | 25.5 |

TABLE 16

Sputum pharmacokinetics for inhaled CIP in CF patients

| | Dose | | | |
|---|---|---|---|---|
| | 50 mg CIP (32.5 mg ciprofloxacin) N = 6 | | 100 mg CIP (65 mg ciprofloxacin) N = 4 | |
| Parameter | Geometric Mean | Geometric CV (%) | Geometric Mean | Geometric CV (%) |
| AUC (mg * h/L) | 72.5 | 179.4 | 472 | 323.8 |
| $C_{max}$ (mg/L) | 33.0 | 443.5 | 200 | 1013.5 |
| $t_{max}$ (h) | 0.98 | 0.8-2.50 | 0.92 | 0.85-1.43 |
| $t_{1/2}$ (h) | 9.04 | 45.0 | 5.53 | 40.7 |
| MRT (h) | 3.02 | 48.5 | 4.00 | 79.1 |

Although the present invention has been described in considerable detail with regard to certain preferred versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A powder composition for pulmonary administration in a unit dose receptacle, the powder composition comprising: particles comprising a ciprofloxacin betaine hydrate and an excipient, wherein the particles have a mass median aerodynamic diameter from about 1 µm to about 5 µm and wherein the ciprofloxacin has a half life in the lungs of at least 1.5 hours, and wherein the composition has a rugosity of from about 3 to 10 and wherein the mass of the composition in the unit dose receptacle is sufficient to provide at least about a 10 mg dose to the lungs of a human patient in three inhalations or less.

2. A composition according to claim 1 wherein the ciprofloxacin betaine hydrate is in crystalline form.

3. A composition according to claim 1 wherein the ciprofloxacin betaine hydrate is ciprofloxacin betaine 3.5 hydrate.

4. A composition according to claim 1 wherein the composition provides an emitted dose in a passive dry powder inhaler of at least about 50%.

5. A composition according to claim 1 in a unit dose receptacle wherein the mass of the composition in the unit dose receptacle is sufficient to provide at least about a 16 mg dose to the lungs in three inhalations or less.

6. A composition according to claim 1 wherein the composition in the unit dose receptacle comprises at least about 16 mg of ciprofloxacin betaine hydrate.

7. A composition according to claim 1 wherein the excipient comprises a phospholipid, a metal ion or both.

8. A composition according to claim 5 wherein the receptacle contains a therapeutic dose of the composition for treating cystic fibrosis.

9. A composition according to claim 1 wherein the particles have a bulk density of less than 0.6 g/cm$^3$.

10. A composition according to claim 1 wherein the composition comprises from 50% to 70% ciprofloxacin betaine hydrate, from 15% to 35% phospholipid, and from 1% to 3% metal ion containing material.

11. A composition according to claim 1 wherein the unit dose receptacle comprises a capsule.

12. A composition according to claim 11 wherein the capsule comprises hydroxypropylmethylcellulose (HPMC).

13. A composition according to claim 1 in combination with a dry powder aerosolization apparatus.

14. A composition and apparatus according to claim 13 wherein the dry powder aerosolization apparatus is adapted to aerosolize the composition within the apparatus by the flow of air through the apparatus.

15. A composition and apparatus according to claim 14 wherein the flow of air is caused by the patient's inhalation.

16. A composition according to claim 1 wherein the mass of the composition in the unit dose receptacle is sufficient to provide at least about a 10 mg dose to the lungs in a single inhalation.

17. A powder composition for pulmonary administration, the powder composition comprising:
particles comprising ciprofloxacin betaine 3.5 hydrate and an excipient, wherein the composition comprises from 50% to 70% ciprofloxacin betaine 3.5 hydrate;
wherein the particles have a mass median aerodynamic diameter from about 1 µm to about 5 µm and wherein the ciprofloxacin has a half life in the lungs of at least 1.5 hours, and
wherein the composition has a rugosity of from about 3 to 10.

18. A composition according to claim 17 wherein the composition provides an emitted dose in a passive dry powder inhaler of at least about 50%.

19. A composition according to claim 17 in a unit dose receptacle wherein the mass of the composition in the unit dose receptacle is sufficient to provide at least about a 10 mg dose to the lungs.

20. A composition according to claim 17 wherein the excipient comprises a phospholipid, a metal ion or both.

21. A composition according to claim 17 wherein the particles have a bulk density of less than 0.6 g/cm$^3$.

22. A composition according to claim 17 wherein the composition comprises from 15% to 35% phospholipid, and from 1% to 3% metal ion containing material.

* * * * *